US007803565B1

(12) United States Patent
Frucht et al.

(10) Patent No.: US 7,803,565 B1
(45) Date of Patent: Sep. 28, 2010

(54) USE OF LYMPHOCYTES TO MEASURE ANTHRAX LETHAL TOXIN ACTIVITY

(75) Inventors: David M. Frucht, Vienna, VA (US); Hui Fang, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 441 days.

(21) Appl. No.: 11/399,003

(22) Filed: Apr. 5, 2006

Related U.S. Application Data

(60) Provisional application No. 60/668,752, filed on Apr. 5, 2005.

(51) Int. Cl.
| | |
|---|---|
| G01N 33/00 | (2006.01) |
| G01N 33/53 | (2006.01) |
| G01N 33/569 | (2006.01) |
| G01N 33/573 | (2006.01) |
| C12N 5/07 | (2010.01) |
| C12N 5/16 | (2006.01) |

(52) U.S. Cl. .................... 435/7.24; 435/4; 435/7.1; 435/7.2; 435/7.32; 435/7.4; 435/7.8; 435/7.92; 435/7.95; 435/23; 435/39; 435/183; 435/219; 435/338; 435/340; 435/343.1; 435/343.2

(58) Field of Classification Search .................... None
See application file for complete search history.

(56) References Cited

U.S. PATENT DOCUMENTS

| | | | |
|---|---|---|---|
| 6,316,197 B1 * | 11/2001 | Das et al. .................... 435/6 |
| 2003/0096333 A1 | 5/2003 | Duesbery et al. | |
| 2003/0224403 A1 | 12/2003 | Popov et al. | |

OTHER PUBLICATIONS

Paccani et al. JEM. Feb. 2005. vol. 201(3):325-331.*
Panchal et al. Jan. 2004. vol. 11(1):67-72.*
DeSilva et al., (J. of Immunology. 1998. vol. 160(9):4175-4181).*
Popov et al., (FEBS Letters. vol. 527:211-215).*
Ivins et al., (Vaccine. 1996. vol. 16(11/12)1142-1148).*
Rontani et al. 1997. FEMS Microbio. Letters. vol. 157:285-289.*
Agrawal and Pulendran, "Anthrax Lethal Toxin: a Weapon of Multisystem Destruction," *Cell. Mol. Life Sci.* 61:2859-2865 (2004).
Cui et al., "Lethality During Continuous Anthrax Lethal Toxin Infusion is Associated with Circulatory Shock but not Inflammatory Cytokine or Nitric Oxide Release in Rats," *Am. J. Physiol. Regul. Integr. Comp. Physiol.* 286:R699-R709 (2004).

(Continued)

*Primary Examiner*—Robert B Mondesi
*Assistant Examiner*—JaNa Hines
(74) *Attorney, Agent, or Firm*—Klarquist Sparkman, LLP

(57) ABSTRACT

It is disclosed herein that isolated lymphocytes, such as human B-cells and CD4$^+$ T-cell can be used to determine an amount of lymphocyte-associated anthrax lethal toxin activity present. Methods of using isolated lymphocytes to identify anthrax therapeutic agents and to determine the efficacy of a potential anthrax therapeutic are disclosed. Methods are also provided for diagnosing and treating anthrax infections.

32 Claims, 15 Drawing Sheets

OTHER PUBLICATIONS

Duesbery et al., Suppression of ras-Mediated Transformation and Inhibition of Tumor Growth and Angiogenesis by Anthrax Lethal Factor, a Proteolytic Inhibitor of Multiple MEK Pathways, *Proc. Natl. Acad. Sci. USA* 98:4089-4094 (2001).

Fang et al., "Anthrax Lethal Toxin Blocks MAPK Kinase-Dependent IL-2 Production in $CD4^+$ T Cells," *J. Immunol.* 174:4966-4971 (2005).

Fang et al., "New Cytokine Markers for the Activity of Anthrax Lethal Toxin," http://www.asmbiodefense.org/2005tueabs.asp, Mar. 22, 2005 (Abstract).

Guidi-Rontani et al., "Anthrax Lethal Toxin-Induced Mitogenic Response of Human T-Cells," *FEMS Microbiol. Lett.* 157:285-289 (1997).

Ivins et al., "Comparative Efficacy of Experimental Anthrax Vaccine Candidates Against Inhalation Anthrax in Rhesus Macaques," *Vaccine* 16:1141-1148 (1998).

Jernigan et al., "Bioterrorism-Related Inhalational Anthrax: The First 10 Cases Reported in the United States," *Emerg. Infect. Dis.* 7:933-944 (2001).

Mourez et al., "2001: A Year of Major Advances in Anthrax Toxin Research," *Trends Microbiol.* 10:287-293 (2002).

Paccani et al., "Anthrax Toxins Suppress T lymphocyte Activation by Disrupting Antigen Receptor Signaling," *JEM* 201:325-331 (2005).

Popov et al., "Effect of *Bacillus anthracis* Lethal Toxin on Human Peripheral Blood Mononuclear Cells," *FEBS Lett.* 527:211-215 (2002).

* cited by examiner

Fig. 2D

NF-κB-Luciferase Reporter

| Anthrax LT | - | - | + | + |
| PMA /Ionomycin | - | + | - | + |

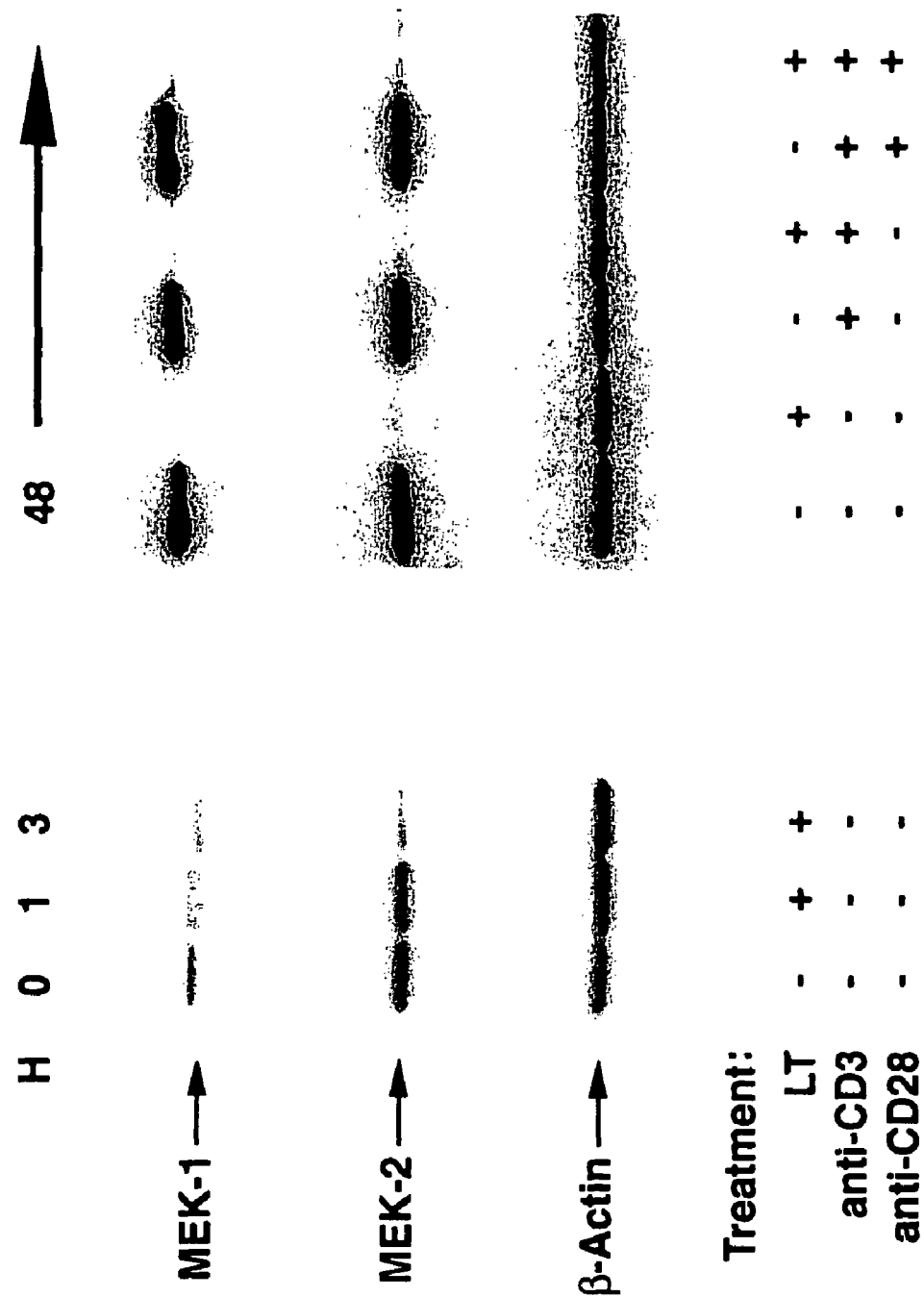

USE OF LYMPHOCYTES TO MEASURE ANTHRAX LETHAL TOXIN ACTIVITY

CROSS-REFERENCE TO RELATED APPLICATIONS

This application claims priority to U.S. Provisional Application No. 60/668,752 filed Apr. 5, 2005, herein incorporated by reference.

FIELD

This application relates to methods of determining the efficacy of an anti-anthrax therapeutic, as well as methods of diagnosing and treating anthrax infections.

BACKGROUND

*Bacillus anthracis* infection is primarily a disease of cattle, but humans can acquire the infection following contact with infected animal products or soil (Mourez et al. *Trends Microbiol.* 10:287, 2002). Despite the relatively low numbers of naturally occurring infections in the U.S. (Jernigan et al., *Emerg. Infect. Dis.* 7:933, 2001), *Bacillus anthracis* is a deadly and efficient bioterrorism agent, as demonstrated by the anthrax attacks in late 2001. Efforts are underway to develop and to stockpile therapeutics for the treatment of established anthrax infection to confront this serious threat to public health (Fox, *Nat. Biotechnol.* 21:216, 2003). To this end, anthrax toxin components have been used as therapeutic targets (Greenfield and Bronze, *Curr. Opin. Investig. Drugs* 5:135, 2004), as these bacterial proteins are virulence factors for *Bacillus anthracis*. These toxin components include lethal factor (LF), edema factor (EF), and protective antigen (PA). Anthrax PA forms pores in cells, thereby permitting intracellular transport of the active toxin enzymes, EF and LF.

Technical challenges currently reduce the ability to identify anthrax therapeutics. For example, in vivo efficacy testing is currently performed in animal models of anthrax infection, due to the low national incidence of naturally-occurring anthrax infection in humans (Chang et al., *Emerg. Infect. Dis.* 9:556, 2003). However, in vitro assays for anthrax toxin activity are needed that closely reflect the in vivo effects of the toxin during human infection. Although in vitro assays are currently available for measuring anthrax LT activity, such assays are limited because they are based on the species- and strain-specific action of the toxin to lyse and/or to inhibit proliferation of BALB/c-derived murine macrophage lines (Hering et al., *Biologicals* 32:17, 2004). These cytotoxic actions of anthrax LT that are cell-, strain-, and species-specific have not been demonstrated to occur in human cells.

Therefore, there is a need for bioassays based on human cell parameters that can be used to screen for agents that reduce anthrax LT activity.

SUMMARY

It is disclosed herein that proliferation of lymphocytes and production of mitogen-activated protein kinase kinase (MAPKK)-dependent cytokines by stimulated T-cells, inversely correlate with anthrax lethal toxin (LT) levels in human cell assays. For example, it is demonstrated that LT is a potent inhibitor of the MAPKK-dependent upregulation of IL-2 production by Jurkat cells, a $CD4^+$ T cell tumor line. Moreover, anthrax LT blocks production of MAPKK-dependent cytokines (such as IL-2, IL-4 and IFN-γ) and IL-2-dependent proliferation by primary human $CD4^+$ T cells following T-cell receptor (TCR) stimulation. Based on these observations, disclosed herein are bioassays that can be used to determine the activity of anthrax LT. In one example, the bioassays use isolated lymphocytes, such as human $CD4^+$ T-cells or human B-cells. Such methods can be used to identify therapeutic agents to treat or prevent anthrax. Also provided are methods of determining an amount of biologically active anthrax LT present in a subject, for example to diagnose anthrax infection.

Based on the observation that anthrax LT can reduce proliferation of stimulated human $CD4^+$ T cells, reduce proliferation of human B cells, and reduce production of MAPKK-dependent cytokines by stimulated human $CD4^+$ T cells, novel bioassays for anthrax biological activity and therapeutic targets are disclosed. In particular examples, the disclosed in vitro methods more closely correlate with toxin-induced pathology in humans than previous methods, such as those using mouse macrophages.

Methods are disclosed for determining the efficacy of a potential anti-anthrax therapeutic, or identifying an agent that decreases the pathogenicity of anthrax, such as an agent that targets anthrax LT. In particular examples, the method includes exposing a lymphocyte (such as an isolated human lymphocyte) to anthrax LT (for example purified anthrax LT or *B. anthracis* spores) and one or more test agents (such as at least one, at least two, at least three, or at least four test agents), and determining whether lymphocyte-associated LT activity is decreased, wherein a decrease in such activity indicates the test agent decreases pathogenicity of anthrax. In some examples, the lymphocyte is an isolated human lymphocyte, such as a cell line growing in culture, or a lymphocyte isolated from a human subject growing in culture.

In particular examples, the lymphocyte is a T-cell (such as a $CD4^+$ T cell), and the method further includes stimulating the T-cell, for example following exposure to anthrax LT. T-cells, in particular examples, include a primary $CD4^+$ T cell obtained from a human subject, or a $CD4^+$ T cell line, such as the Jurkat cell line or derivative thereof. Stimulation includes contacting T-cells with an agent that permits initiation of an immune response by the T-cell, such as secretion of IL-2. Methods of stimulating T-cells are known in the art. For example, the TCR of a $CD4^+$ T cell can be stimulated using anti-CD3 agents (alone or in combination with a co-stimulatory molecule, such as an anti-CD28 agent). Alternatively, TCR/CD28 costimulation can be mimicked by PMA plus $Ca^{2+}$ ionophore (such as ionomycin).

In another example, the lymphocyte is a B-cell and the method further includes stimulating the B-cell, for example following exposure to anthrax LT. Stimulation includes contacting B-cells with an agent that permits initiation of a response by the B-cell, such as initiating cell proliferation or secretion of immunoglobulins. Methods of stimulating B-cells are known in the art. In some examples, a B-cell is exposed to an activated helper T-cell or an agent that cross-links surface immunoglobulins (Igs). In particular examples, the B-cell receptor (BCR) of a B cell is stimulated using LPS, anti-CD40, anti-IgM, pokeweed mitogen, liposomes decorated with Fab' fragments of anti-human IgM antibodies (immunoliposomes; for example see Furukawa et al., *J. Immunol. Meth.* 131:105-12, 1990), or combinations thereof. In some examples, a B-cell is stimulated via the BCR and co-stimulated with CD21/CD21L.

In one example, the lymphocyte (for example a stimulated lymphocyte) is first contacted with anthrax LT prior to contacting the cell with the test agent. The anthrax LT can be either purified or isolated LT, or it can be present in a more diluted form, for example in or produced by an anthrax organism. In a particular example, the lymphocyte contacted with the test agent during or before stimulation of the lymphocyte.

In one example, lymphocyte-associated LT activity is determined by measuring the functional effect of LT. Examples of LT functional activity include but are not limited to, the effect of LT on one or more MAPKK-dependent cytokine responses to LT. Examples of MAPKK-dependent cytokine responses to LT include, but are not limited to: the production of a MAPKK-dependent cytokine by activated T-cells (such as $CD4^+$ cells), the production of a MAPKK-dependent cytokine by activated B-cells, and the effect of a MAPKK-dependent cytokine on downstream effects (such as lymphocyte proliferation, for example proliferation of activated T-cells or activated B-cells). In some examples, the effect of LT on lymphocyte proliferation, such as B-cell proliferation, occurs independently of the biological activity of a MAPKK-dependent cytokine.

In particular examples, lymphocyte-associated LT activity is determined by detecting one or more MAPKK-dependent cytokine responses to LT. For example, the response can be determined by measuring an amount of MAPKK-dependent cytokine (such as IL-2, IL-4, IFN-γ, or combinations thereof) secreted into the supernatant from a stimulated T- or B-cell, wherein a decrease in the amount of MAPKK-dependent cytokine produced by the stimulated lymphocyte indicates the presence of lymphocyte-associated LT activity. In another particular example, lymphocyte-associated LT activity is determined by measuring lymphocyte proliferation, such as proliferation of a stimulated B-cell or a stimulated T-cell, wherein a decrease in proliferation indicates the presence of lymphocyte-associated LT activity.

In particular examples, the method further includes comparing the observed lymphocyte-associated LT activity in the presence of the test agent to a control, baseline, or reference value (such as a standard curve). For example, the lymphocyte-associated LT activity in the presence of the test agent can be compared to a baseline obtained prior to addition of the test agent. In some examples, the observed lymphocyte-associated LT activity is compared to lymphocyte-associated LT activity in the presence of a control, such as a positive or negative control. An example of a positive control is a cell (or a sample from such a cell) exposed to an agent known to decrease anthrax pathogenicity (such as a neutralizing antibody to anthrax LT), wherein similar (or reduced) lymphocyte-associated LT activity relative to the positive control indicates the test agent decreases pathogenicity of anthrax. An example of a negative control is a cell (or a sample obtained from such a cell) infected with anthrax LT and an agent known to not affect anthrax pathogenicity, wherein decreased lymphocyte-associated LT activity relative to the negative control indicates the test agent decreases pathogenicity of anthrax. In yet another example, the observed lymphocyte-associated LT activity is compared to a reference value, such as an amount of lymphocyte proliferation or amount of one or more MAPPK-dependent cytokines in the presence (or absence) of LT.

In particular examples, the disclosed methods are conducted in vitro (such as in a cell culture). In addition, an agent observed in vitro to have a therapeutic effect on anthrax infection can be subsequently screened in vivo to further assess the efficacy of the potential anti-anthrax agent. For example, the agent observed in vitro to decrease lymphocyte-associated LT activity can be administered to a subject, such as a laboratory animal, to determine whether such activity is decreased in the subject, wherein a decrease in lymphocyte-associated LT activity indicates the agent that decreased lymphocyte-associated LT activity decreases pathogenicity of anthrax. Exemplary laboratory animals include non-human primates (such as cynomolgus monkeys and rhesus macaques), as well as rodents (such as mice, rats, rabbits and guinea pigs). In one example, determining whether lymphocyte-associated LT activity is decreased in the subject includes determining whether lymphocyte-associated LT activity is decreased in a sample obtained from the subject (such as a blood sample or fraction thereof), for example using the methods described herein.

Methods for treating anthrax are also disclosed. For example, anthrax infection is treated by interfering with or otherwise offsetting the LT-associated effects on lymphocytes. Alternatively, anthrax infection is treated or avoided by administering to a subject (such as a human) of a therapeutically effective amount of an agent found to decrease the biological activity of LT using the assays disclosed herein, for example by neutralizing anthrax LT. In one example, the method includes decreasing lymphocyte-associated LT activity in the subject, for example by administering a therapeutically effective amount of an agent found to decrease the biological activity of LT using the assays disclosed herein. In one example, such a therapeutic agent increases the biological activity of one or more MAPKK-dependent cytokines, for example by increasing the amount of such cytokines produced by activated T-cells or B-cells in the subject, for example by increasing the mRNA or protein levels of a MAPKK-dependent cytokine (such as IL-2, IL-4, IL-6, or IFN-γ). In some examples, such a therapeutic agent increases proliferation of lymphocytes in the subject, for example thereby increasing the number of B-cells or T-cells in the subject. Increasing lymphocyte production can enhance protective immune responses to the anthrax infection. In particular examples, such methods reduce systemic shock during anthrax infection.

Also provided by the present disclosure are methods of determining an amount of lymphocyte-associated LT activity present in a subject, for example to diagnose an anthrax infection in a subject (such as infection with *B. anthracis* or a spore thereof or exposure to anthrax LT). Such a method permits detection of biologically active LT (for example in contrast to an assay that only permits detection of LT but does not indicate whether the LT is active or neutralized). In particular examples, the method includes determining whether such LT activity is increased in a sample obtained from the subject, wherein an increase in lymphocyte-associated LT activity indicates the subject is infected with anthrax. In one example, lymphocyte-associated LT activity is assessed by contacting an isolated lymphocyte with a sample obtained from the subject (such as a sample that may contain anthrax LT), and determining whether the lymphocytes display activity associated with exposure to LT, for example by measuring the activity of a MAPKK-dependent cytokine. In a particular example, lymphocyte-associated LT activity is determined by measuring an amount of MAPKK-dependent cytokine secreted by an activated B-cell or T-cell following exposure to a sample from the subject. Measuring an amount of a cytokine can be, for example, through a direct quantitation or indirect assessment based on its functional activity. In a particular example, the activity of a MAPKK-dependent cytokine is determined by assessing lymphocyte proliferation.

In particular examples, determining whether the lymphocytes display activity associated with exposure to LT includes comparing the observed lymphocyte-associated LT activity in the subject to a baseline, control, or reference value (such as a standard curve). For example, the observed amount of MAPKK-dependent cytokine production can be compared to a standard curve showing the amount of MAPKK-dependent cytokine production (such as an amount of IL-2 production) in the presence of particular amounts of biologically active LT. This permits a determination of the amount of biologically active LT present in the subject. If detectable biologically active LT is present in the subject, this indicates that the subject has been exposed to anthrax LT, for example by infection with anthrax spores. In some examples, specificity is established using a neutralizing antibody to anthrax LT, which will reverse anthrax-dependent LT activity, thereby restoring MAPKK-dependent cytokine production.

The foregoing and other objects, features, and advantages of the disclosure will become more apparent from the following detailed description, which proceeds with reference to the accompanying figures.

BRIEF DESCRIPTION OF THE DRAWINGS

FIG. 2D is a bar graph showing the effect of anthrax LT on PMA-induced activity of NF-κB. Representative experiments from three separate experiments are shown. Error shown represents intra-assay standard deviation generated from triplicate samples.

FIG. 4A is a digital image of a Western blot showing the total MEK-1, MEK-2, and β-actin levels (loading control) present in human $CD4^+$ T cells cultured in the presence or absence of anthrax LT, anti-CD3, or anti-CD3/CD28.

DETAILED DESCRIPTION

Abbreviations and Terms

Figure 1A:
FIG. 1A is a digital image of a Western blot showing the decrease of MAPKK-dependent signaling in anthrax LT-treated Jurkat cells. Jurkat cell cultures were treated with anthrax LT for the amount time indicated. Total MEK-1 levels (upper panel), MEK-2 levels (middle panel), and β-actin levels (loading control, lower panel) are shown.
Figure 1A:
Figure 1A:
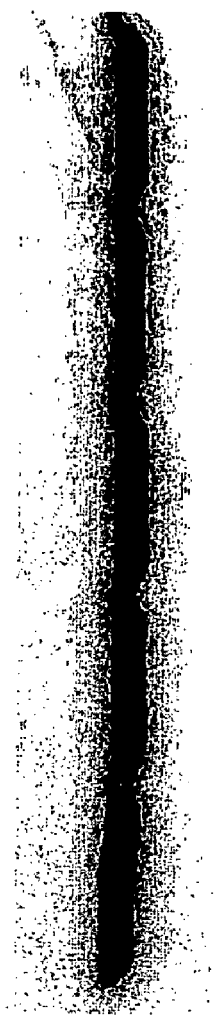

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a test agent" includes single or plural test agents and is considered equivalent to the phrase "comprising at least one test agent" or to the phase "comprising one or more test agents." The term "or" refers to a single element of stated alternative elements or a combination of two or more elements, unless the context clearly indicates otherwise. For example, the phrase "decreases production of a MAPPK-dependent cytokine or decreases cell proliferation" refers to a decrease in production of a MAPPK-dependent cytokine, a decrease in cell proliferation, or a combination of both a decrease in production of a MAPPK-dependent cytokine and a decrease in cell proliferation. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

IL-2: interleukin 2
IL-4: interleukin 4
IFN-γ: interferon gamma
LT: anthrax lethal toxin
MAPKK: mitogen-activated protein kinase kinase
PMA: 12-O tetradecanoylphorbol 13-acetate
TCR: T cell receptor Anthrax disease: The disease caused by the bacterium *Bacillus anthracis*. Anthrax disease occurs when *B. anthracis* spores enter the body, germinate to the bacillary form, and multiply. The disease can take on one of four forms: (1) Cutaneous, the most common, results from contact with an infected animal or animal products; (2) Inhalational is much less common and a result of spore deposition in the lungs, while (3) Gastrointestinal and (4) Oropharyngeal (back of the throat) are due to ingestion of infected meat. Cutaneous disease constitutes the majority (up to 95%) of anthrax cases. Anthrax usually develops in cattle, horses, sheep, and goats. Anthrax in humans is rare unless the spores are spread intentionally.

The average incubation period for anthrax is 1 to 7 days, but it can take 60 days or longer for symptoms to develop. Symptoms depend on how the infection was acquired. For example, cutaneous anthrax has the following characteristics. Skin infection begins as a small, raised bump that might itch. Within 1 to 2 days, the bump develops into a fluid-filled blister about 1 cm (0.4 in.) to 3 cm (1.2 in.) in diameter. Within 7 to 10 days, the blister usually has a black center of dying tissue (eschar) surrounded by redness and swelling. The blister is usually painless. Additional blisters may develop.

Anthrax toxin: An exotoxin produced by most strains of *B. anthracis*. In its native form, the toxin consists of three heat-labile, antigenically distinct components: lethal factor (LF), protective antigen (PA) and edema factor (EF), which in concert lead to some of the clinical effects of anthrax. All three genes are encoded by the plasmid pXO1. Together, LF and PA constitute the lethal toxin (LT), and EF and PA the edema toxin.

Although the native anthrax toxin includes LF, PA, and EF, as used herein the term "anthrax toxin" can also refer to a toxin that does not include EF (that is, one that includes LF and PA (known as LT)).

B-cell (or B lymphocyte): A lymphocyte derived from bone marrow that provides humoral immunity; it recognizes free antigen molecules in solution and matures into plasma cells that secrete immunoglobulin (antibodies) that inactivate the antigens. B-cells are characterized by the presence of surface immunoglobulin, monomeric IgM or IgD. When stimulated by antigen, B-cells proliferate and differentiate into plasma cells and memory B-cells.

B-cell stimulation (or activation): A state in which a B-cell response (such as proliferation or secretion of immunoglobulins) has been initiated or activated by a signal, such as by interaction with an activated helper T-cell or by cross-linking of surface immunoglobulins (Igs) by antigen or anti-Ig. Stimulating the B-cell antigen receptor (BCR) initiates a cascade of signal transduction events, including activation of cytoplasmic protein tyrosine kinase (PTK) and rapid increase in cytoplasmic free calcium.

Stimulation of B-cells can be detected, for example, by [$^3$H]-uridine incorporation into RNA (as B-cells differentiate, RNA synthesis increases), or by [$^3$H]-thymidine incorporation, which measures DNA synthesis associated with cell proliferation. Alternatively, B-cell activation can be measured as a function of immunoglobulin secretion.

*Bacillus anthracis*: A spore-forming Gram-positive bacteria that causes anthrax.

CD4$^+$ T lymphocyte (or CD4$^+$ T Cell): A white blood cell that carries a marker on its surface known as "cluster of differentiation 4" (CD4). These cells, also known as helper T cells, help orchestrate the immune response, including antibody responses as well as killer T-cell responses.

Decrease: To reduce, for example to reduce the amount or other measure of activity of something, for example as compared to a control. When the term "decrease" is used herein, a 100% decrease is not required. Therefore, the term can refer to decreases of at least 20%, at least 40%, at least 50%, at least 60%, at least 75%, at least 80%, at least 90%, at least 95%, at least 98%, or even at least 100%. In particular examples, the amount of decrease is compared to a baseline or a control, such as an amount of lymphocyte-associated LT activity present in a lymphocyte not exposed to anthrax LT.

Diagnose: To determine whether a subject has a disease or disorder, such as an anthrax disease. A disease can be diagnosed, for example, based on signs or symptoms associated with the disease, such as a laboratory result (for example one that determines an amount of lymphocyte-associated LT activity present in a subject).

Infect: The introduction of a pathogen (or a portion thereof) into a host cell, such as a cell of a subject. In a particular example, infection includes introduction of anthrax into a lymphocyte, or administration to a subject, such as in the form of *B. anthracis* spores or anthrax LT.

IL-2 (interleukin 2): A cytokine that plays a role in T-cell proliferation and cellular immunity (O'Shea et al., *Nat Rev Immunol* 2:37, 2002). Release of IL-2 by stimulated T-cells results in activation and differentiation of other T-cells independently of antigen. IL-2 is considered to be a central regulator of immune responses (Waguespack et al., *Brain. Res. Bull.* 34: 103-9, 1994). In particular examples, under physiological conditions IL-2 is produced by CD4$^+$ T-cells following activation of the TCR, for example with mitogens or allogens.

IL-2 includes an IL-2 peptide or nucleic acid sequence from any organism, including variants, fragments, and fusions thereof that retain full or partial IL-2 biological activity. Human IL-2 is synthesized as a precursor protein of 153 amino acids with the first 20 amino terminal amino acids functioning as a hydrophobic secretory signal sequence.

IL-2 nucleic acid and protein sequences for many species are known in the art. For example, IL-2 sequences are publicly available from GenBank Accession Nos. S82692 (human cDNA), AAB46883 and AAD14263 (human protein), U19847 (rhesus monkey cDNA), AAB60400 (rhesus monkey protein), NM_053836 (rat cDNA), and NP_000575 (rat protein). IL-2 can include functional homologs, such as natural variants.

Methods for detecting IL-2 are known in the art, and include, but are not limited to, determining an amount of IL-2 protein (such as by using ELISA or Western blotting) or nucleic acid (such as by RT-PCR; Brandt et al. 1986. *Lymphokine Research* 5: S35-S42; Lindquist et al. 1988. *J. Immunol. Meth.* 113: 231-5) present, or detecting a biological activity of IL-2 associated with the presence of a particular level of IL-2.

IL-4: A cytokine produced by activated T-cells that promotes antibody production by causing proliferation and differentiation of B-cells. IL-4 includes an IL-4 peptide or nucleic acid sequence from any organism, including variants, fragments, and fusions thereof that retain full or partial IL-4 biological activity. Human IL-4 is a 129 amino acid protein (20 kDa) synthesized as a precursor containing a hydrophobic secretory signal sequence of 24 amino acids.

IL-4 nucleic acid and protein sequences for many species are known in the art. For example, IL-4 sequences are publicly available from GenBank Accession Nos. X81851 (human cDNA), CAA57444 (human protein), AF457197 (rhesus monkey cDNA), AAN76987 (rhesus monkey protein), AY496861 (rat cDNA), and AAR87867 (rat protein). IL-4 can include functional homologs, such as natural variants.

Methods for detecting IL-4 are known in the art, and include but are not limited to, determining an amount of IL-4 protein (such as by using ELISA or Western blotting) or nucleic acid (such as by RT-PCR; Boulay and Paul. *Cur. Opin.*

*Immunol.* 4:294-8, 1992; Paul and Ohara. *Ann. Rev. Immunol.* 5:429-59, 1987) present. IL-4 can also be detected, and even quantitated, by measuring a biological activity associated with IL-4. In a specific example, a B-cell co-stimulation assay is used to measure the enhanced proliferation of stimulated purified B-cells due to the presence of IL-4. IL-4 can be detected also in bioassays, employing IL-4-responsive cells (such as BALM-4, BCL1, CCL-185, and CT.4S). A specific detection method for human IL-4 is the induction of CD3 in B-cell lines with CD23 detected for example, using flow-through cytometry or a fluorescence immunoassay.

Interferon-gamma (IFN-γ): An interferon produced by T-cells in response to TCR stimulation (for example stimulation with antigens, mitogens, or alloantigens). The synthesis of IFN-γ is induced, among other things, by IL-2, β-FGF, and EGF.

IFN-γ includes an IFN-γ peptide or nucleic acid sequence from any organism, including variants, fragments, and fusions thereof that retain full or partial IFN-γ biological activity. Human IFN-γ is a dimeric protein glycosylated at two sites with subunits of 146 amino acids. At least six variants of naturally occurring IFN-γ have been described, and differ from each other by variable lengths of the C-terminal ends.

IFN-γ nucleic acid and protein sequences for many species are known in the art. For example, IFN-γ sequences are publicly available from GenBank Accession Nos. NM_000619 (human cDNA), NP_000610 (human protein), AY376145 (rhesus monkey cDNA), and AAQ87963 (rhesus monkey protein). IFN-γ can include functional homologs, such as natural variants.

Methods of detecting IFN-γ are known in the art, and include but are not limited to, determining an amount of IFN-γ protein using an immunoassay (such as a Western blot or ELISA) or nucleic acid molecule (for example by using RT-PCR) present. IFN-γ can also be detected, and even quantitated, by measuring a biological activity associated with IFN-γ. The induction of the synthesis of IP-10 can also be used to measure IFN-γ concentrations. Another bioassay employs induction of indoleamine 2,3-dioxygenase activity in 2D9 cells. A sensitive radioreceptor assay is also available. In addition, minute amounts of IFN-γ can be detected indirectly by measuring IFN-induced proteins such as Mx protein.

Isolated: An "isolated" biological component (such as a nucleic acid molecule, protein or portion of hematological material, such as blood components) has been substantially separated or purified away from other biological components of the organism in which the component naturally occurs. For example, nucleic acids and proteins that have been "isolated" include nucleic acids and proteins purified by standard purification methods. The term also embraces nucleic acids and proteins prepared by recombinant expression and those prepared using chemical synthesis.

An isolated cell is one that has been substantially separated or purified away from other biological components of the organism in which the cell naturally occurs, such as other cells of the organism. For example, an isolated lymphocyte cell population is a population of lymphocytes that is substantially separated or purified away from other blood cells, such as red blood cells. In a particular example, an isolated $CD4^+$ cell population is a population of $CD4^+$ cells that is substantially separated or purified away from other blood cells, such as $CD8^+$ cells. In one example, an isolated $CD4^+$ T-cell population is at least 95% pure, such as at least 99% pure. In another particular example, an isolated B-cell population is a population of B-cells that is substantially separated or purified away from other blood cells, such as T-cells. In one example, an isolated B-cell population is at least 95% pure, such as at least 99% pure.

LF (lethal factor): A metalloprotease that cleaves the mitogen-activated protein kinase kinases (MAPKKs), including MEK1, MEK2, MKK3, MKK4, MKK6 and MKK7, but not MEK5, thereby inhibiting the MAPK pathway. Lethal factor is pathogenic enzyme of anthrax. Includes native LF nucleic acid and protein sequences (such as those that are abut 90 kD), as well as variants, fragments, and fusions thereof that retain full or partial LF biological activity. Also includes recombinantly produced LF.

LT (anthrax lethal toxin): A multimer of protective antigen (PA) and lethal factor (LF). Also referred to in the art as LeTx. LT is a virulence factor for *Bacillus anthracis* whose biological activity includes the ability to proteolyticly cleave and inactivate MAPKKs that propagate pro-survival signals in macrophages. In particular examples, LT is sufficient to induce one or more the laboratory manifestations of anthrax disease in vitro (such as in a tissue culture system), or in vivo (such as in non-human primates and rodents). Includes native LT nucleic acid and protein sequences, as well as variants, fragments, and fusions thereof that retain full or partial LT biological activity. Also includes recombinantly produced LT.

LT activity: Refers to the activity of anthrax LT that induces one or more pathological effects in response to infection with anthrax LT, such as the pathological effects that occur to lymphocytes in culture treated with anthrax LT. Such effects can be mediated by immunological, toxic, or other pathological mechanisms.

Methods of decreasing LT activity include, but are not limited to, increasing expression of a MAPKK-dependent cytokine (such as IL-2, IL-4, or IFN-γ) protein or nucleic acid sequence (such as decreasing transcription or translation), as well as increasing lymphocyte proliferation.

Lymphocyte: Any of the mononuclear, nonphagocytic leukocytes found in the blood, lymph, and lymphoid tissues, that are involved in the immune defenses of the body. Lymphocytes are generally divided into two classes, B-cells and T-cells, which are responsible for humoral and cellular immunity, respectively.

Lymphocyte-associated LT activity: Refers to effects LT has on lymphocytes. Examples of this activity include, but are not limited to, the ability of LT to decrease the biological activity of a MAPKK-dependent cytokine (for example by decreasing production of a MAPKK-dependent cytokine by an activated T-cell or by decreasing lymphocyte proliferation) such as IL-2, IL-4, or IFN-γ, or the ability of LT to decrease proliferation of a lymphocyte (such as an activated T cell or a B-cell).

MAPKK (mitogen-activated protein kinase kinases): A family of protein kinases that are part of the MAPK (also known as ERK) signal transduction pathway. These kinases are activated by diverse stimuli such as growth factors, cytokines, neurotransmitters and various cellular stresses.

MAPKK-dependent cytokine: A cytokine whose production depends on MAPKK activation, for example MAPKK activation in a lymphocyte. Examples include, but are not limited to: TNF-α, IL-1α, IL-1β, IL-2, IL-4, IL-6, IL-12, IL-18, IFN-γ, or combinations thereof. In a particular example, a MAPKK-dependent cytokine is one not ordinarily found in a macrophage or dendritic cell.

Pathogenicity or pathological activity of anthrax: The ability of *B. anthracis* or a portion thereof (such as anthrax LT) to inflict damage to a cell (such as a lymphocyte) by any mechanism, for example to cause disease in a subject.

Pharmaceutical agent or drug: A chemical compound or composition capable of inducing a desired therapeutic or prophylactic effect when administered to a subject, alone or in combination with another therapeutic agent(s) or pharmaceutically acceptable carriers. In a particular example, a pharmaceutical agent decreases one or more symptoms of an anthrax infection.

Proliferation: An increase in the amount of something, for example by reproduction or multiplication. For example, cell proliferation is the increase the growth or production of cells. In a particular example, lymphoproliferation is an increase in the production of lymphocytes, such as an increase in the number of T-cell (for example $CD4^+$ T-cells) or B-cells.

Protective antigen (PA): One of the three proteins that comprise the anthrax toxin and one of the two proteins that constitutes LT. Native PA is an 83 kD protein so named because it is the main protective constituent of anthrax vaccines. PA binds to the anthrax toxin receptor (ATR) on target cells and is then proteolytically cleaved by the enzyme furin of a 20 kd fragment. The smaller cleaved 63 kD PA remnant ($PA_{63}$) oligomerizes features a newly exposed, second binding domain and binds to either EF to form edema toxin, or LF to form lethal toxin (LT), and the complex is internalized into the cell. From these endosomes, the $PA_{63}$ channel enables translocation of LF and EF to the cytosol.

Includes native PA nucleic acid and protein sequences, as well as variants, fragments, and fusions thereof that retain PA biological activity. Also includes recombinantly produced PA.

Purified: The term purified does not require absolute purity; rather, it is a relative term. Thus, for example, a purified peptide preparation is one in which the peptide is more enriched than the peptide is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide.

In one example, an anthrax LT peptide is purified when at least 60% by weight of a sample is composed of LT, for example when 75%, 95%, or 99% or more of a sample is composed of LT. Examples of methods that can be used to purify proteins, include, but are not limited to the methods disclosed in Sambrook et al. (Molecular Cloning: A Laboratory Manual, Cold Spring Harbor, N.Y., 1989, Ch. 17). Protein purity can be determined by, for example, polyacrylamide gel electrophoresis of a protein sample, followed by visualization of a single polypeptide band upon staining the polyacrylamide gel; high-pressure liquid chromatography; sequencing; or other conventional methods.

Sample: A biological specimen, such as one that contains nucleic acid molecules (such as cDNA or mRNA), proteins, or combinations thereof. Exemplary samples include, but are not limited to: peripheral blood, plasma, serum, urine, saliva, tissue biopsy, pulmonary washings, expectorated sputum, surgical specimen, amniocentesis samples and autopsy material. In one example, a sample includes lymphocytes, such as B-cells or T-cells, or subpopulations thereof (for example a $CD4^+$ T-cell).

Subject: Living multi-cellular vertebrate organisms, including human and veterinary subjects. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Supernatant: The medium in which a cell is grown. The supernatant includes material secreted by the cell into the medium, such as secreted cytokines. In a particular example, a supernatant includes serum obtained from a subject.

T-Cell (or T lymphocytes): A thymocyte-derived lymphocyte that expresses the T-cell receptor (TCR) and is responsible for cell-mediated immunity. In the presence of transforming agents (mitogens) or antigens, T lymphocytes differentiate and divide. These cells have characteristic CD3 surface markers and can be further divided into subsets according to function. For example, T-cells include, but are not limited to, $CD4^+$ T-cells and $CD8^+$ T cells.

T-cell stimulation (or activation): A state in which a T-cell response has been initiated or activated by a primary signal, such as through the TCR/CD3 complex, or via interaction with a protein antigen. A T-cell is activated if it has received a primary signaling event that initiates an immune response by the T cell, such as secretion of IL-2. T-cell stimulation includes stimulation of a T cell with a primary signal (such as anti-CD3 or anti-CD2), alone or in combination with a co-stimulatory molecule (such as anti-CD28).

Test agent: A candidate agent (including chemical compounds and compositions, as well as biological agents, such as antibodies) that is tested to determine its activity, such its effect on lymphocyte-associated anthrax LT activity or a symptom of anthrax disease.

Therapeutically Effective Amount: An amount of a pharmaceutical preparation that alone, or together with a pharmaceutically acceptable carrier or one or more additional therapeutic agents, induces the desired response. The preparations disclosed herein are administered in therapeutically effective amounts.

In one example, it is an amount sufficient to partially or completely alleviate or avoid symptoms of anthrax infection within a subject. Treatment can involve only slowing the progression of the infection temporarily, but can also include halting or reversing the progression of the infection permanently. For example, a pharmaceutical preparation can decrease one or more symptoms of anthrax, for example decrease a symptom by at least 20%, at least 50%, at least 70%, at least 90%, at least 98%, or even at least 100%, as compared to an amount in the absence of the pharmaceutical preparation.

Effective amounts a therapeutic agent can be determined in many different ways, such as assaying for a reduction in the rate of infection of cells or subjects or improvement of physiological condition of an infected subject. Effective amounts also can be determined through various in vitro, in vivo or in situ assays, including the assays described herein.

Therapeutic agents can be administered in a single dose, or in several doses, for example daily, during a course of treatment. However, the effective amount of can be dependent on the source applied (for example a vaccine isolated from a cellular extract versus a chemically synthesized and purified vaccine), the subject being treated, the severity and type of the condition being treated, and the manner of administration.

Treatment: A therapeutic intervention that either improves or inhibits (including preventing) a disease, such as anthrax. For example, a treatment can ameliorate a sign or symptom of a disease or pathological condition, such a sign or symptom of anthrax disease. Treatment can also induce remission or cure of a condition, such as anthrax disease. In one example, a treatment inhibits the full development of a disease, for example preventing development of anthrax disease. However, preventing a disease does not require a total absence of infection. For example, a decrease of at least 50% can be sufficient.

Vaccine: An antigenic preparation that can be administered to a mammal to stimulate the recipient's humoral and cellular immune systems to one or more antigens present in the vaccine preparation. Vaccine compositions can include proteins or polysaccharides, and can further include an adjuvant. In one particular example, a vaccine includes anthrax LT or a portion thereof.

Assays for Determining Lymphocyte-Associated Anthrax Lethal Toxin Activity

As the primary cell targets for infection by Bacillus anthracis, the emphasis of anthrax research has centered on macrophages. Anthrax LT protease cleaves MAPKKs (Vitale et al., J. Appl. Microbiol. 87:288, 1999), which are components of the signal transduction pathways involved in the activation of macrophages in response to bacterial components and to pro-inflammatory cytokines. By disabling these pro-inflammatory pathways, it has been proposed that B. anthracis is able to avoid containment by macrophages and, ultimately, overwhelms its host (Fukao, Lancet Infect. Dis. 4:166, 2004).

It is shown herein for the first time that lymphocytes, such as CD4$^+$ T cells and B cells, are direct targets for anthrax LT. Degradation of MAPKKs by anthrax LT renders human CD4$^+$ T cells unable to respond normally to signaling through the T-cell receptor (TCR). For example, anthrax LT reduces the ability of human CD4$^+$ T cells to produce MAPKK-dependent cytokines (such as IL-2, IL-4 and IFN-γ) in response to stimulation through their antigen receptors. It is also shown herein that anthrax LT cleaves and inactivates MAPKKs in the human CD4$^+$ T cell line, Jurkat. This, in turn, leads to the specific blockade of the MAPKK signaling pathways in response to TCR stimulation and the dose-dependent inhibition of TCR-dependent IL-2 production. Based on these observations in lymphocytes, methods are disclosed for measuring the activity of lymphocyte-associated anthrax LT activity. In particular examples, such methods are used to assess potency of therapeutics that target anthrax LT.

It is shown herein that anthrax LT has direct effects on the cells regulating adaptive immunity. The effects of anthrax LT on both innate and adaptive immune responses may act in synergy to paralyze overall immune responses in infected hosts. The combined effects of MAPKK signal transduction blockade in many types of cells, including non-immune cells, may be responsible for many of the late-stage sequelae of anthrax infection.

Based on the observation that anthrax LT has a direct effect on suppressing production of IL-2, a central cytokine in adaptive immune responses, as well as suppressing production of other MAPKK-dependent cytokines (such as IL-4 and IFN-γ), and suppressing proliferation of lymphocytes, bioassays for evaluating potential anti-anthrax therapeutics are disclosed. Such assays can be used to determine whether a test agent can decrease the pathogenicity of anthrax, for example to identify agents that have the potential to treat a subject having an anthrax infection or to prevent anthrax infection. The disclosed assays can also be used to determine the efficacy or potency of an agent suspected of having anti-anthrax activity. In one example, such assays can be conducted in vitro, such as using isolated cells in culture, such as an isolated human lymphocyte.

In one example, the method includes contacting an isolated lymphocyte with anthrax LT (for example in the form of a B. anthracis spore or purified anthrax LT) and one or more test agents (such as at least one test agent, at least two test agents, or at least three test agents), and determining whether lymphocyte-associated LT activity is reduced, wherein a decrease in such LT activity indicates the test agent decreases pathogenicity of anthrax, for example by decreasing the biological activity of anthrax LT.

Examples of lymphocytes include B-cells and T-cells, such as CD4$^+$ T cells. The cells can be primary cells, such as those obtained from a subject (such as from a blood sample), or can be cell lines, such as Jurkat cells. Other lymphocyte cell lines, such as CD4$^+$ T cell lines, are known in the art, such as those available from ATCC (Manassas, Va.). In one example, the lymphocyte is a stimulated lymphocyte. For example, the lymphocyte can in certain examples be a stimulated B-cell or a stimulated T-cell, such as a stimulated CD4$^+$ T cell. For example, the method can include providing a stimulated lymphocyte, or stimulating the lymphocyte.

A T-cell is stimulated if it has received a signal that can initiate an immune response by the T-cell, such as production of IL-2. In one example, a T-cell is stimulated by a primary signal, such as via the TCR/CD3 complex, or via interaction with a protein antigen. Methods of stimulating T-cells are known in the art, and are discussed in more detail below. In particular examples the T-cell is stimulated ex vivo (for example in a cell culture) by contacting the T-cell with an agent that activates the T-cell receptor (TCR), such as an anti-CD3 antibody. In some examples, stimulation of the T-cell further includes contacting the T-cell with an agent that co-stimulates the T-cell, such as an anti-CD28 antibody. In one example, a T-cell is stimulated with one or more agents that mimic TCR stimulation. For example, T-cells can be stimulated by contacting the cell with an agent that mobilizes intracellular stores of calcium (such as ionomycin) and an agent that activates protein kinase C (such as PMA).

A B-cell is activated if it has received a signal that can initiate a response by the B-cell, such as initiating proliferation of the B-cell or secretion of Ig molecules from the B-cell. In one example, a B-cell is stimulated by contacting the cell with an activated helper T-cell or an agent that cross-links surface Ig. Methods of stimulating B-cells are known in the art, and are discussed in more detail below. In particular examples the B-cell is stimulated ex vivo (for example in a cell culture) by contacting the B-cell with an agent that activates the B-cell receptor (BCR). In some examples, stimulation of the B-cell further includes contacting the B-cell with an agent that co-stimulates the B-cell, such as CD21/CD21L.

In one example, lymphocyte-associated LT activity is determined by measuring the biological activity of LT, for example by detecting a MAPKK-dependent cytokine response to the LT. Methods of detecting a MAPKK-dependent cytokine are known in the art, and can include measuring an amount of MAPKK-dependent cytokine produced by a lymphocyte, or measuring a downstream MAPKK-dependent cytokine effect, such as an amount of lymphocyte proliferation.

For example, the amount of B-cell or primary CD4$^+$ T cell proliferation can be measured, wherein an increase in proliferation in the presence of the test agent (for example as compared to an amount of proliferation in the presence of LT and absence of test agent) indicates that the lymphocyte-associated LT activity is decreased and that the test agent decreases pathogenicity of anthrax. Alternatively, if the amount of proliferation is compared to an amount of proliferation in the absence of the test agent and the absence of LT, and a similar amount of proliferation is observed, this indicates that the lymphocyte-associated LT activity is decreased and that the test agent decreases pathogenicity of anthrax. Methods of determining an amount of cell proliferation are known, and include [$^3$H] thymidine uptake assays.

In one example, detecting a MAPKK-dependent cytokine response to LT includes determining an amount of MAPKK-dependent cytokine produced by a T-cell or a B-cell. For example, an amount of extracellular MAPKK-dependent cytokine, such as IL-2, IL-4, or IFN-γ, released into a T-cell culture medium can be determined. In another example, an amount of extracellular MAPKK-dependent cytokine, such as IL-6, TNF-α, and IL-1, released into a B-cell culture medium can be determined. Methods for determining whether a particular protein is present are known in the art. In another example, the MAPKK-dependent cytokine is detected by measuring the effect of a MAPKK-dependent cytokine on another cell or protein.

In particular examples, the method further includes comparing the observed lymphocyte-associated LT activity in the presence of the test agent to a control, baseline, or reference value (such as a standard curve). For example, the observed lymphocyte-associated LT activity in the presence of the test agent can be compared to an established baseline or a reference standard. For example, a reference standard can be a value representing an amount of lymphocyte-associated LT activity present relative to a particular experimental value, such as an amount of MAPKK-dependent cytokine or an amount of lymphocyte proliferation. By comparing the experimental value measured to the reference standard, the amount of lymphocyte-associated LT activity can be determined. In another example, the observed lymphocyte-associated LT activity is compared to lymphocyte-associated LT activity in the presence of a control, such as a positive or negative control.

An example of a positive control is one that contains an amount of lymphocyte-associated LT activity present (such as the functional activity, for example an amount of cell proliferation or amount of secreted MAPKK-dependent cytokine) when cells are infected with LT and contacted with an agent known to decrease anthrax pathogenicity (such as a neutralizing antibody to anthrax LT). For example, the control can include an amount of cell proliferation or an amount of MAPKK-dependent cytokine (such as an amount of IL-2, IL-4, IL-6, or IFN-γ). When comparing the lymphocyte-associated LT activity present in the experimental to the positive control, similar or even reduced lymphocyte-associated LT activity relative to the positive control indicates the test agent decreases pathogenicity of anthrax. For example, when comparing the lymphocyte-associated LT activity present in the experimental to the positive control, similar or increased cell proliferation or MAPKK-dependent cytokine activity (such as an amount of secretion of such a cytokine) relative to the positive control indicates the test agent decreases pathogenicity of anthrax. In contrast, an increase in lymphocyte-associated LT activity (such as a decrease in cell proliferation or other MAPKK-dependent cytokine activity) relative to the positive control indicates the test agent does not significantly decrease pathogenicity of anthrax. For example, a test agent that results in lymphocyte-associated LT activity (such as the functional activity or amount of MAPKK-dependent cytokine, such as an amount of lymphoproliferation) that is similar to that observed in the positive control, such as a difference of no more than 20%, no more than 10%, or no more than 5%, indicates that the agent is a potential anti-anthrax therapeutic, which can be used in particular examples to treat or prevent an anthrax infection (for example to reduce systemic shock or inflammation).

An example of a negative control is one that contains an amount of lymphocyte-associated LT activity (such as the functional activity or amount of MAPKK-dependent cytokine, such as an amount of cell proliferation) present in anthrax LT-infected cells contacted with an agent known to not affect anthrax pathogenicity (such as PBS). For example, the control can include an amount of proliferation or amount of a MAPKK-dependent cytokine (such as an amount of IL-2, IL-4, IL-6, or IFN-γ) present when no potentially therapeutic test agent is included. When comparing the lymphocyte-associated LT activity present in the experimental to the negative control, decreased lymphocyte-associated LT activity relative to the negative control indicates the test agent decreases pathogenicity of anthrax. For example, a test agent that decreases or eliminates lymphocyte-associated LT activity, for example by increasing cell proliferation or increasing MAPKK-dependent cytokine activity (such as an amount of secretion of such a cytokine) relative to the negative control indicates the test agent decreases pathogenicity of anthrax. In one example, a test agent that results in lymphocyte-associated LT activity (such as the functional activity or amount of MAPKK-dependent cytokine, such as amount of lymphoproliferation) that is decreased relative to that observed in the positive control, such as a decrease of at least 10%, at least 50%, at least 90%, or even at least 99% as compared to the negative control, can be used in particular examples to treat or prevent an anthrax infection or to inhibit (such as prevent) anthrax infection.

In some examples, the method includes comparing the observed lymphocyte-associated LT activity in the presence of the test agent to a standard curve, wherein the standard curve represents an amount of lymphocyte-associated LT activity versus an amount of biologically active LT present. By determining where on the curve the experimental lymphocyte-associated LT activity falls, the amount of biologically active LT present can be determined.

In one example, lymphocytes are contacted with the anthrax LT prior to contacting the cell with the test agent. In another example, the lymphocyte is a stimulated lymphocyte, and the lymphocyte is contacted with the test agent during or before stimulating the T-cell or B-cell.

To determine if a test agent can treat anthrax infection, the following exemplary methods can be used. In one example, isolated lymphocytes (for example a lymphocyte growing in culture) are contacted with one or more test agents, and the cells subsequently (or at the same time as the test agent) exposed to anthrax LT. In one example, the lymphocytes are exposed to anthrax LT and contacted with the test agent simultaneously. In a particular example, the lymphocytes are exposed to anthrax LT at least 5 minutes after contact with the test agent, such as at least 10 minutes, at least 30 minutes, at least 60 minutes, or even at least 120 minutes after contacting the lymphocytes with the test agent. In some examples, multiple time points are determined. In another example, the method includes contacting an exposing an isolated lymphocyte to anthrax LT and subsequently to one or more test agents. In some examples, the cells are contacted with the test agent at least 5 minutes after infection with LT, such as at least 10 minutes, at least 30 minutes, at least 60 minutes, or even at least 120 minutes after anthrax LT exposure. In some examples, multiple time points are determined. In particular examples, following exposure to anthrax LT and the test agent, the lymphocytes are stimulated.

Following exposure to anthrax LT and the test agent (and in some examples following lymphocyte stimulation), lymphocyte-associated LT activity is determined, such as at least 15 minutes, at least 30 minutes, at least 60 minutes, at least 2 hours, or even at least 24 hours following exposure. In some examples, multiple time points are determined. Methods of determining lymphocyte-associated LT activity include, but are not limited to, measuring functional activity of LT, for example by detecting a MAPKK-dependent cytokine response to the LT, such as measuring an amount of MAPKK-dependent cytokine or an amount of lymphocyte proliferation. The method can further include comparing lymphocyte-associated LT activity to a baseline, control or reference value. Agents that decrease lymphocyte-associated LT activity (such as those that increase MAPKK-dependent cytokine activity, such as increase an amount of lymphocyte proliferation) can be useful, for example, in treating (including avoiding) anthrax infection. In some examples, such agents reduce one or more symptoms of systemic shock.

In particular examples, a human lymphocyte in culture is infected with anthrax LT for at least 10 minutes, at least 30 minutes, at least one hour, at least four hours, at least six hours, or even for at least 24 hours. Exemplary amounts of LT include, but are not limited to, a ratio of at least 1:1 of PA:LF, for example 2:1 PA:LF, 2.5:1 PA:LF, or even 4:1 PA:LF.

In particular examples, the method further includes testing in vivo those test agents that had anti-anthrax LT effects in vitro. In one example, the method includes selecting one or more test agents that decreased lymphocyte-associated LT activity in the disclosed assays, administering the identified agent to a subject, determining whether lymphocyte-associated LT activity is decreased in the subject, wherein a decrease in lymphocyte-associated LT activity indicates the agent that decreased lymphocyte-associated LT activity decreases pathogenicity of anthrax. In a particular example, determining whether lymphocyte-associated LT activity is decreased includes determining whether lymphocyte-associated LT activity is decreased in a sample obtained from the subject (such as a lymphocyte or serum from the subject). Exemplary subjects include, but are not limited to, a laboratory animal, such as a non-human primate (for example a rhesus macaque or cynomolgus macaque) or other mammals, such as a rodent (for example a rat, mouse, rabbit, or guinea pig). In a specific example, the subject is a human subject.

In particular examples determining lymphocyte-associated LT activity in the subject includes detecting a MAPKK-dependent cytokine (such as the activity of IL-2, IL-4, IL-6, or IFN-γ) response to the LT in a sample obtained from the subject. The lymphocyte-associated LT activity that is detected is a measure of potential biological activity that LT can induce. In a particular example, determining lymphocyte-associated LT activity in the subject includes determining an amount of MAPKK-dependent cytokine (such as the amount of IL-2, IL-4, IL-6, or IFN-γ) present in a sample obtained from the subject. For example, extracellular amounts of IL-2, IL-4, IL-6 or IFN-γ can be determined from a serum or plasma sample obtained from the subject. In another example, determining lymphocyte-associated LT activity in the subject includes determining an amount of lymphocyte proliferation in the subject, for example by determining the number of lymphocytes present in a sample obtained from the subject.

In one example, lymphocyte-associated LT activity in the subject is determined by exposing sera obtained from the subject to an isolated lymphocyte, such as a lymphocyte in culture. The resulting lymphocyte-associated LT activity is then determined, wherein the presence of lymphocyte-associated LT activity indicates that biologically active TL is present in the subject. In particular examples, the resulting lymphocyte-associated LT activity is compared to a baseline, control, or reference value (such as a standard curve).

Lymphocytes

Lymphocytes that can be used in the disclosed bioassays, for example when the bioassay is an in vitro assay, are known. Ideally, the lymphocytes used are susceptible to anthrax LT, and show an increase in lymphocyte-associated LT activity (such as a decrease in lymphoproliferation or a decrease in the production of one or more MAPKK-dependent-cytokines) following exposure to anthrax LT. In a particular example, the lymphocyte is isolated, such that the population of lymphocytes substantially includes lymphocytes (or a sub-population thereof, such as $CD4^+$ T cells). For example, the lymphocyte can be a primary lymphocyte, such as one obtained from a subject, such as a human subject. In one example, the isolated lymphocyte is a cell line, such as Jurkat or derivatives thereof, as well as human T-cell lines generated through HTLV-1 transformation.

In one example, the cell is a human lymphocyte, such as a commercially available cell line or a primary cell line derived from a subject. In particular examples, a lymphocyte population or sub-population thereof (such as a B-cell or T-cell population, for example a $CD4^+$ T cell population), is at least 90% pure, such as at least 95% pure or at least 99% pure.

In one example, the cell is a B-cell. B-cell lines and methods of obtaining B-cells from a blood sample are known in the art. For example, B-cells can be isolated from peripheral blood obtained from a mammal, such as a human. In one example, mononuclear cells are separated from heparinized peripheral blood. Enriched B-cells can be obtained from the mononuclear cells by immunomagnetic isolation (for example using Dynabeads M450 Pan-B-CD19, Dyna A.S., Oslo, Norway), or using negative or positive selection immunomagnets (Miltenyi).

In another example, the cell is a T-cell, such as a $CD4^+$ T-cell. T-cell lines and methods of obtaining T cells from a blood sample are known in the art. For example, the Jurkat $CD4^+$ T cell line (American Type Culture Collection) can be used.

In one example, a $CD4^+$ T-cell is obtained from a mammal, such as a human subject. Methods for purification of $CD4^+$ T-cell from blood are known. Although particular exemplary methods are described herein, the disclosure is not limited to these methods. In one example, $CD4^+$ T-cells are isolated via cell sorting. One specific, non-limiting example of a method of isolating $CD4^+$ cells is the use of negative magnetic immunoadherence. This method uses a cocktail of monoclonal antibodies directed to cell surface markers present on the cells negatively selected. For example, to isolate cells, a monoclonal antibody cocktail can include antibodies to CD14 (such as monoclonal antibody 63D3, or 20.3), CD20 (such as monoclonal antibody IF5 or Leu-16), CD11b (such as monoclonal antibody OKMI or 60.1), CD16 (such as monoclonal antibody FC-2.2 or 3G8), HLA-DR (such as monoclonal antibody 20.6 or HB10a and CD8 (such as monoclonal antibody OKT8, 51.1, or G10-1.1). This process of negative selection results in an essentially homogenous population of $CD4^+$ cells (see U.S. Pat. No. 5,858,358).

Another exemplary method that can be used to isolate $CD4^+$ T-cells from a blood sample is a two-step purification procedure. Human $CD4^+$ T-cells can be prepared from buffy coats as follows. The buffy coat product is incubated with RosetteSep Human $CD4^+$ Cell Enrichment Cocktail (StemCell Technologies; Vancouver, Canada). The sample is then diluted with an equal volume of PBS with 2% FBS. $CD4^+$ T cells are isolated by negative selection following separation through a Ficoll gradient (non-$CD4^+$ cells were sedimented).

Stimulation of Lymphocytes

Methods of stimulating lymphocytes are known in the art. Although particular exemplary methods are described herein, the disclosure is not limited to these methods. Lymphocytes can be stimulated one or more times, for example one or two times. In particular examples, lymphocytes are stimulated following exposure to anthrax LT.

In one example, a purified population of CD4+ T-cells is stimulated by activating the TCR/CD3 complex, alone or in combination with induction of a second, costimulatory signal. For example, the TCR/CD3 complex can be activated by contacting the cells with an anti-CD3 antibody. Examples of anti-human CD3 monoclonal antibodies that can be used are OKT3 (American Type Culture Collection, Manassas, Va.) and G19-4. Similarly, binding of an anti-CD2 antibody will activate T cells. In a particular example, CD4+ T-cells are stimulated by contacting the cells with an anti-CD3 antibody, alone or in the presence of an antibody that specifically binds to a T-cell costimulatory molecule. In one example, the antibodies are immobilized, for example on a bead, a magnetic solid phase surface, or adhered to a tissue culture flask. In a particular example, the CD4+-T cells are incubated with an anti-CD3 antibody for at least five minutes, such as at least one hour, at least four hours, or at least 24 hours.

In one example, co-stimulation is achieved by contacting the cells with a molecule that activates an accessory molecule on the surface of the T-cell (such as CD28), for example by using a ligand which binds the accessory molecule (such as a member of the B7 family of proteins, such as B7-1 (CD80) and B7-2 (CD86)) or an antibody that specifically binds the accessory molecule (such as an anti-CD28 monoclonal antibody or fragment thereof capable of cross-linking CD28). Anti-CD28 antibodies or fragments thereof that can be used are known in the art, and include, but are not limited to: monoclonal antibody 9.3 (Bristol Myers Squibb Corporation, Seattle, Wash.), monoclonal antibody KOLT-2, 15E8, 248.23.2, and EX5.3D10 (see U.S. Pat. No. 5,858,358).

T-cell costimulatory molecules include, but are not limited to: CD28; inducible costimulatory molecule (ICOS); 4-1BB receptor (CDw137); lymphocyte function-associated antigen-1 (LFA-1); CD30; and CD154 (for example see Salomon and Bluestone, *Ann. Rev. Immunol.* 19:225-52, 2001). Methods of stimulation of T-cells with immobilized anti-CD3 and an immobilized costimulatory molecule are known (see U.S. Pat. No. 3,858,350 and PCT WO 94/29436).

In another particular example, CD4+ T-cells are stimulated with a combination of agents that mimic TCR stimulation, such as agents that mobilize intracellular stores of calcium (such as ionomycin) and agents that activate protein kinase C (such as PMA). For example, CD4+-T cells can be incubated in the presence of ionomycin and PMA for an amount of time that permits stimulation, such as at least 2 hours, such as at least 24 hours.

In one example, a purified population of B-cells is stimulated by contacting the cell with an agent that permits initiation of a response by the B-cell, such as an activated helper T-cell or an agent that cross-links surface Ig. In particular examples the B-cell is contacted with an agent that activates the B-cell receptor (BCR), such as LPS, anti-CD40, anti-IgM, pokeweed mitogen, liposomes decorated with Fab' fragments of anti-human IgM antibodies, or combinations thereof. In some examples, stimulation of the B-cell further includes contacting the B-cell with an agent that co-stimulates the B-cell, such as CD21/CD21L.

Test Agents

Exemplary test agents include, but are not limited to, any peptide or non-peptide composition in a purified or non-purified form, such as peptides made of D- and/or L-configuration amino acids (in, for example, the form of random peptide libraries; see Lam et al., *Nature* 354:82-4, 1991), phosphopeptides (such as in the form of random or partially degenerate, directed phosphopeptide libraries; see, for example, Songyang et al., *Cell* 72:767-78, 1993), nucleic acid molecules, antibodies (such a monoclonal, polyclonal, chimeric, and humanized antibodies, or a fragment thereof), and small or large organic or inorganic molecules such as aromatics, fatty acids, and carbohydrates. A test agent can also include a complex mixture or "cocktail" of molecules.

In a particular example, a test agent is a vaccine preparation that promotes a host immune response against anthrax LT (for example a peptide, such as an anthrax LT peptide or portion thereof, and an adjuvant).

In a particular example, a test agent is an agent that decreases or inhibits lymphocyte-associated LT functional activity (for example an agent that increases MAPKK-dependent cytokine activity, such as lymphocyte proliferation). Such agents can include those that increase transcription or translation of one or more MAPKK-dependent cytokines (such as IL-2, IL-4, IL-6, or IFN-γ). Examples of such agents include, but are not limited to, a nucleic acid sequence encoding a MAPKK-dependent cytokine (or functional portion thereof), or a MAPKK-dependent cytokine protein. Other examples of such agents include, but are not limited to, agents that increase lymphocyte proliferation, such as proliferation of a stimulated $CD4^+$ T-cell or B-cell (for example CpG oligos and anti-CD40). In another example, the test agent is a neutralizing antibody, such as one that binds to LT and neutralizes lymphocyte-associated anthrax LT activity.

Anthrax LT

Lymphocytes can be exposed to anthrax toxin, for example by incubating the cells with the toxin. In one example, a purified tripartite exotoxin is used. In another example, a combination of LF and PA is used. Recombinant PA and LF are commercially available (see Example 1). The physiological receptor binding ratio is 7 PA molecules to 3 LF molecules. However other ratios can be used. Exemplary ratios of PA:LF include, but are not limited to, at least 1:1 PA:LF, at least 2:1 PA:LF, at least 2.5:1 PA:LF, or even at least 4:1 PA:LF. In a particular example, at least 0.001 μg/ml LF and at least 0.001 μg/ml of PA are contacted with the cells, such as at least 0.01 μg/ml LF and at least 0.01 μg/ml of PA, at least 0.1 μg/ml LF and at least 0.1 μg/ml of PA, or at least 1 μg/ml LF and at least 1 μg/ml of PA. In another particular example, at least 10 μg LF and at least 10 μg of PA are administered to a subject, such as at least 50 μg LF and at least 50 μg of PA, or at least 100 μg LF and at least 100 μg of PA. In yet another example, at least 0.01 μg LF per g of subject (μg/g) and at least 0.01 μg/g of PA are administered to a subject, such as at least 0.1 μg/g LF and at least 0.1 μg/g of PA, or at least 0.5 μg/g LF and at least 0.5 μg/g of PA.

Measuring Lymphocyte-Associated LT Activity

Methods for determining lymphocyte-associated LT activity (including pathological activity) are known in the art. Although exemplary methods are provided herein, the disclosure is not limited to such methods. For example, lymphocyte-associated LT activity can be determined by detecting one or more MAPKK-dependent cytokine responses to LT, such as the activity of IL-2, IL-4, IL-6 or IFN-γ, or a downstream effect of MAPKK-dependent cytokine activity, such as lymphocyte proliferation.

In one example, one or more MAPKK-dependent cytokines are detected by measuring an amount of one or more MAPKK-dependent cytokines present. For example, an amount of MAPKK-dependent cytokine released by a lymphocyte (for example into the culture medium or into the serum or plasma of a subject) can be determined, such as by detecting such secreted cytokines using an immunoassay (for example by Western blotting or by ELISA).

In one example, antibodies specific for MAPKK-dependent cytokines (such as IL-2, IL-4, IL-6, and IFN-γ) permit detection of these proteins in the supernatant. Antibodies that are specific for MAPKK-dependent cytokines (such as IL-2, IL-4, IL-6, and IFN-γ) are known in the art. For example, incubation of serum or a lymphocyte supernatant with the antibodies permits formation of protein-antibody complexes. The presence of such complexes can be determined using methods known in the art. For example, the antibody can include a detectable label, such as a fluorophore, radiolabel, or enzyme, which permits detection of the antibody, for example using ELISA. In particular examples, multiple antibodies (each with a unique detectable label) are incubated with the supernatant, and the presence of multiple complexes detected simultaneously.

In a particular example, Western blotting is used to detect the presence of MAPKK-dependent cytokines, such as those present in a lymphocyte culture supernatant or those present in an extracellular fluid of a subject (such as serum). Briefly, the lymphocyte supernatant or extracellular fluid is resolved by SDS-PAGE, and the proteins transferred to an appropriate medium, such as nitrocellulose. The nitrocellulose is incubated with the appropriate antibody (which itself can have a label, or which can be detected by using the appropriate labeled secondary antibody), which permits detection of the antibody-protein complex.

In another example, a colorimetric assay is used to detect the presence of MAPKK-dependent cytokines (such as IL-2, IL-4, IL-6, and IFN-γ) present in a solution, such as those present in a lymphocyte culture supernatant or serum sample. Briefly, the supernatant or serum is exposed to a material that will produce a colorimetric reaction if a MAPKK-dependent cytokine is present, for example at a particular concentration.

In addition to the methods described above, lymphocyte-associated LT activity can be measured by other methods known in the art. For example, quantitative mass spectroscopy can be used to quantitate an amount of MAPKK-dependent cytokine present.

In yet another example, lymphocyte-associated LT activity is measured by detecting (and some examples quantitating) MAPKK-dependent cytokine nucleic acid molecules (such as mRNA and cDNA), for example by RT-PCR. Such methods are known in the art. Briefly, total RNA is isolated (for example with Trizol-LS, Life Technologies), and the RNA reverse transcribed into cDNA (for example using the cDNA Cycle kit for RT-PCR, Invitrogen). The resulting cDNA can be quantified (for example by utilizing the CytoXpress Quantitative PCR kit for human IL-4, Biosource International, Camarillo, Calif.).

In addition to the above methods, other bioassays permit detection of MAPKK-dependent cytokine biological functional activity. For example, IL-4 is a co-stimulator of B-cells. Therefore, methods that include incubation of a lymphocyte culture supernatant (such as lymphocytes previously treated with LT and a test agent) with a purified B-cell, and measuring proliferation of the B-cells, can be used to determine if IL-4 is present. An increase in proliferation of the stimulated B-cells indicates the presence of IL-4. In another example, the presence of IFN-γ can be determined by measuring the indoleamine 2,3-dioxygenase activity in 2D9 cells. Therefore, methods that include incubation of a lymphocyte culture supernatant (such as lymphocyte previously treated with LT and a test agent) with 2D9 cells, and measuring the resulting indoleamine 2,3-dioxygenase activity in the 2D9 cells, can be used to determine if IFN-γ is present. An increase in indoleamine 2,3-dioxygenase activity indicates the presence of IFN-γ. In addition, IFN-γ can be detected indirectly by measuring IFN-induced proteins such as Mx protein.

Lymphocyte-associated LT activity can also be determined by measuring proliferation of lymphocytes, such as proliferation of a B-cell or a T-cell (such as a primary CD4$^+$ T-cell). In one example, the lymphocyte is a stimulated lymphocyte. Methods of measuring cell proliferation are known in the art. Although exemplary methods are provided herein, the disclosure is not limited to such methods. In one example, an assay that measures DNA synthesis is used, such as a tritiated thymidine uptake assay. Briefly, lymphocytes are incubated with [$^3$H]thymidine for a time sufficient to permit incorporation of the into the growing DNA strand. In one example, lymphocytes are incubated with 1 μCi of [$^3$H]thymidine for at least 6 hours, such as at least 12 hours. In another example, a MTT assay is used to measure cell proliferation. Briefly, lymphocytes are incubated with MTT reagent (such as that available from R&D systems) for a period of time sufficient to allow measurement of proliferating cells. For example, the incubation can be terminated when a purple precipitate is visible, for example by microscopy. In one example, the lymphocytes are incubated with the MTT reagent for at least 1 hour, such as at least 2 hours. Lymphocytes are subsequently incubated with detergent, and absorbance at 570 nm determined. Lymphocyte proliferation can also be measured by using the CellTiter 96 Aqueous NonRadioactive Cell Proliferation Assay (Promega) according to the manufacturer's instructions.

In examples where the potential anti-anthrax therapeutic is further assayed in vivo, a sample is obtained from the subject, and the lymphocyte-associated LT activity in the subject determined using the methods described above. For example, a serum sample can be used to measure lymphocyte-associated LT activity present extracellularly, such as an amount of MAPKK-dependent cytokine present in the subject (for example by using ELISA or Western blotting as described above). In another example, a sample containing isolated lymphocytes from the subject (such as isolated B-cells or isolated CD4$^+$ T cells) can be used to measure proliferation of such lymphocytes (for example by determining the total number of lymphocytes in the sample, or by measuring proliferation of such lymphocytes in culture, for example by using the assays discussed above).

In some examples, lymphocyte-associated LT activity observed in an experimental sample is compared to the lymphocyte-associated LT activity observed in the presence of a control sample, such as a sample containing anthrax LT, isolated stimulated lymphocytes, and an anti-anthrax LT neutralizing antibody. The anti-anthrax LT neutralizing antibody can be used as a control to demonstrate specificity, as it will reverse anthrax LT-dependent effects. For example, if the observed lymphocyte-associated LT activity in an experimental sample is similar (or decreased) relative to the to the lymphocyte-associated LT activity observed in the anti-anthrax LT neutralizing antibody containing sample, this indicates that the test agent used in the experimental sample is a potential anti-anthrax therapeutic.

Methods of Treating Anthrax

Methods are provided for treating an anthrax infection, such as a subject exposed to *B. anthracis* (or spores thereof) or exposed to anthrax toxin (such as LT). Such methods can be used to reduce one or more symptoms associated with anthrax infection, such as systemic shock, fever, inflammation, or blisters on the skin. In particular examples, the method includes administering an agent that targets (for example by opposing or reversing) one or more lymphocyte-associated LT effects. Such methods include administering to a subject having an anthrax infection or otherwise exposed to LT a therapeutically effective amount of one or more agents that decrease LT biological activity in the subject, such as in the lymphocytes of the subject. In one example, such an agent is identified using the disclosed assays.

For example, lymphocyte-associated LT biological activity can be decreased or mitigated by increasing the effect of MAPKK-dependent cytokines (such as IL-2, IL-4, IL-6, or IFN-γ) in the subject (for example by increasing the biological activity or amount) or by increasing proliferation of lymphocytes in the subject. In specific examples, the method includes increasing an amount of IL-2, IL-4, IL-4 or IFN-γ present in the subject. In particular examples the method includes specifically increasing the effect of MAPKK-dependent cytokines in the subject.

Similar methods can be used to inhibit (such as prevent) an anthrax infection. For example, subjects at risk of anthrax infection can be administered therapeutically effective amount of one or more agents that decrease LT biological activity in the subject, such as in the lymphocytes of the subject. In one example, such an agent is identified using the disclosed assays.

Methods of Measuring Lymphocyte-Associated Anthrax LT Activity in a Subject

Based on the observation that anthrax LT activity is inversely correlated with the activity of MAPKK-dependent cytokines and lymphocyte proliferation in a dose-dependent manner, methods are disclosed for determining an amount of lymphocyte-associated LT activity present in a subject, for example an amount of biologically active LT present in a subject. Such methods can be used to diagnose an anthrax infection (such as exposure to LT or to B. anthracis spores) in a subject. For example, the presence of detectable lymphocyte-associated LT activity can indicate that the subject has an anthrax infection, or has been exposed to anthrax LT.

In particular examples, such assays can be used to determine an amount of biologically active anthrax LT present in a subject. This is in contrast to assays that can only detect the presence of LT, but cannot distinguish whether the LT is active or has been neutralized. For example, it is possible that a subject exposed to anthrax will have developed antibodies, or will have been treated with a monoclonal antibody that would neutralize anthrax LT activity. In such cases, LT would be present, but not active. In contrast, the disclosed assays can be used to determine whether LT, if present, is also biologically active.

In one example the method includes determining an amount of lymphocyte-associated LT activity present in a sample obtained from the subject, such as a serum sample or a sample that includes isolated lymphocytes (or isolated subpopulations thereof). The observed lymphocyte-associated LT activity can be compared to a baseline, control, standard curve, or other reference value that permits determination of the amount of biologically active LT present in the subject. The amount of lymphocyte-associated LT activity can be determined directly, for example by measuring an amount of MAPKK-dependent cytokine present in a serum sample, or by determining the number of lymphocytes (or subpopulation thereof) in a blood sample. In another example, the amount of lymphocyte-associated LT activity is determined indirectly, for example by contacting a sample from the subject (such as a sample that could contain anthrax LT, for example a serum sample) with an isolated lymphocyte, and comparing an amount of lymphocyte-associated LT activity of the lymphocyte to a baseline, control, standard curve, or other reference value to determine an amount of lymphocyte-associated LT activity present in the subject. For example, proliferation of the lymphocyte could be measured, or an amount of MAPKK-dependent cytokine secreted by the lymphocyte determined. In one example, the control is a negative control sample containing anti-anthrax LT neutralizing antibody. In another example, the reference value is an amount of lymphocyte-associated LT activity (or amount of biologically active LT) in the presence of anti-anthrax LT neutralizing antibody.

In particular examples, the amount of lymphocyte-associated LT activity present is compared to standard curve. An example of a standard curve is a graph that compares an amount of LT to an amount of a particular lymphocyte-associated LT activity (such as an amount of MAPKK-dependent cytokine present or an amount of cell proliferation), wherein the curve permits determining an amount of LT present in the subject.

EXAMPLE 1

Anthrax LT Blocks MAPKK-Dependent Signaling in Jurkat Cells

This example describes methods used to measure MAPKK-dependent signaling following exposure of Jurkat cells to anthrax LT. One skilled in the art will appreciate that other human lymphocytes can be used, such as CD4$^+$ T cells.

Jurkat E6.1 cells (for example from American Type Culture Collection, Manassas, Va.; ATCC Number: TIB-152) were cultured in RPMI complete medium containing 10% FBS (Hyclone; Logan, Utah), 10 mM Hepes buffer, 1 mM sodium pyruvate (Quality Biological; Gaithersburg, Md.), 2 mM l-glutamine (GibcoBRL; Grand Island, N.Y.) and 1% antibiotic/antimycotic (Sigma; St. Louis, Mo.). Cell viability was assessed by trypan blue exclusion.

To demonstrate that anthrax LT cleaves and thus inactivates MAPKKs in Jurkat cells (a human CD4$^+$ T cell line), lysates generated from Jurkat cells treated with anthrax LT were assayed by Western blotting for MEK-1 and MEK-2 (as well as beta-actin as a control) in a time course experiment as follows. Jurkat cell cultures were treated with anthrax LT (anthrax PA and LF, List Biological Laboratories, Inc., Campbell, Calif.) for 0-180 minutes. Unless otherwise indicated, LT treatments were administered in excess at 2.5 μg/mL PA and 1 μg/mL LF.

Following the incubation, 1-2×10$^6$ cells were centrifuged, and the resulting cell pellet lysed on ice for 30 minutes in a buffer containing 20 mM Tris-HCl, 150 mM NaCl, 5 mM EDTA, 2.5 mM sodium pyrophosphate, 1 mM Na$_3$VO$_4$, 1% Triton-X-100, and a protease inhibitor cocktail (Sigma; St. Louis, Mo.). A different buffer was used to lyse samples for PLC-αl Western blotting as previously described (Rellahan et al., *Exp. Cell Res.* 289:184, 2003). Protein extracts were generated from centrifuged lysates, and 55 μg was loaded on a 4-12% NuPage gradient gel (Invitrogen; Carlsbad, Calif.). These protein extracts were electrophoretically separated and then transferred onto 0.2 μm nitrocellulose membranes (Bio-Rad; Hercules, Calif.). Western blotting was performed using standard techniques as previously described (Cordoba-Rodriguez et al., *J. Biol. Chem.* 279:20563, 2004). The following primary antibodies were used for Western blotting assays: anti-MEK1 (BD Biosciences; San Diego, Calif.), anti-MEK2, anti-phospho-PLC-γl, anti-p44/42 MAPK, anti-phospho-p44/42 MAPK, anti-phospho-JNK, anti-JNK, antiphospho-p38 MAPK, and anti-p38 MAPK (Cell Signaling Technology; Beverly, Mass.). Horseradish peroxidase-conjugated anti-rabbit (Amersham Biosciences; Piscataway, N.J.), anti-mouse (Amersham Biosciences), or anti-goat (Abcam; Cambridge, Mass.) antibodies were used as secondary antibodies.

As shown in FIG. 1A, degradation of MEK-1 and MEK-2 was observed starting 30 minutes following anthrax LT treatment, with complete degradation between 2-3 hours.

Figure 1B:
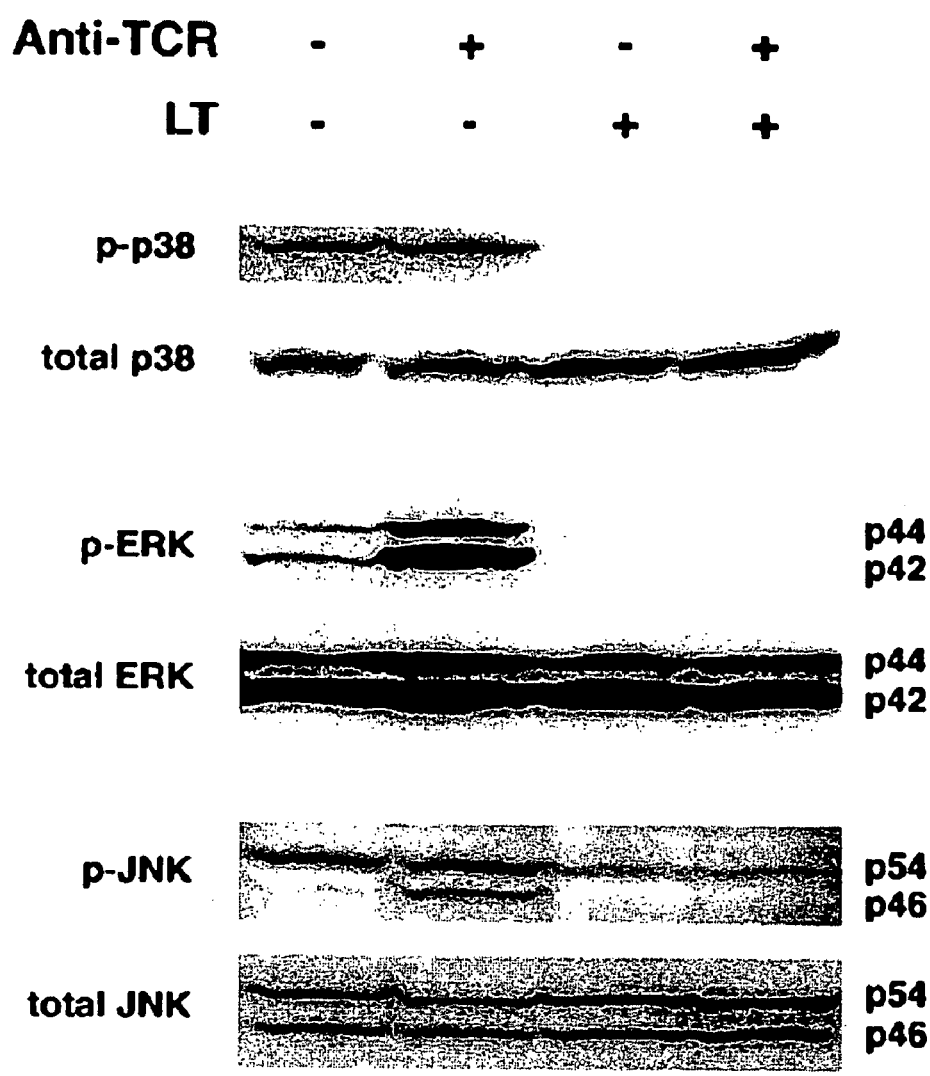
FIG. 1B is a digital image of a Western blot showing a decrease in downstream MAPK targets in anthrax LT-treated Jurkat cells. Levels of phospho-p38, phospho-ERK p44/42, and phospho-JNK p54/46 were assessed by Western blotting. Subsequently, levels of total p38, ERK p44/42, and JNK p54/46 were determined by reblotting these membranes.

To demonstrate that anthrax LT-dependent proteolysis of MAPKKs correlated with the inhibition of signaling to their downstream MAPK targets (ERK, p38 and JNK), Jurkat cells pre-cultured in the presence or absence of anthrax LT were re-stimulated with C305 (a specific Jurkat TCR-activating monoclonal antibody) for five minutes, and western blotting performed as described above. As shown in FIG. 1B, anthrax LT significantly decreased both basal phosphorylation and anti-TCR-induced phosphorylation of p38 (FIG. 1B, upper panel) and p44/p42 ERK (FIG. 1B, middle panel). In addition, anthrax LT significantly decreased basal and anti-TCR-induced phosphorylation of p46 JNK, and partially reduced basal levels of p54 JNK phosphorylation (FIG. 1B, lower panel).

To determine the effect of anthrax LT on TCR- and PMA-induced activity of an AP-1, the following methods were used. Jurkat cells ($10^7$) were transfected with of an AP-1-responsive luciferase construct (pAP1-Luc; BD Biosciences, Palo Alto, Calif.) by electroporation as previously described (Rellahan et al., *J. Exp. Med.* 180:1529, 1994). Cells were cultured overnight in RPMI complete medium ($10^7$ cells/10 mL) and then transferred to 24 well plates and treated in the presence or absence of a specific Jurkat TCR-activating monoclonal antibody (C305), phorbol-12-myristate-13-acetate (PMA), and/or anthrax LT (1 µg/mL LF+2.5 µg/mL PA) for five hours in RPMI complete medium (400 µL). PMA was prepared in DMSO and used at a dose of 50 ng/mL (EMD Biosciences, Inc.; San Diego, Calif.). After stimulation, the cells were centrifuged and the pellet lysed in luciferase reporter buffer (Promega Corporation; Madison, Wis.). A 20 µL portion of each sample lysate was added to 100 µL of the luciferase assay reagent (Promega) and luminescence determined on a Microplate luminometer LB96V (Berthold Technologies GmbH & Co. KG; Bad Wildbad, Germany).

Figure 1C:
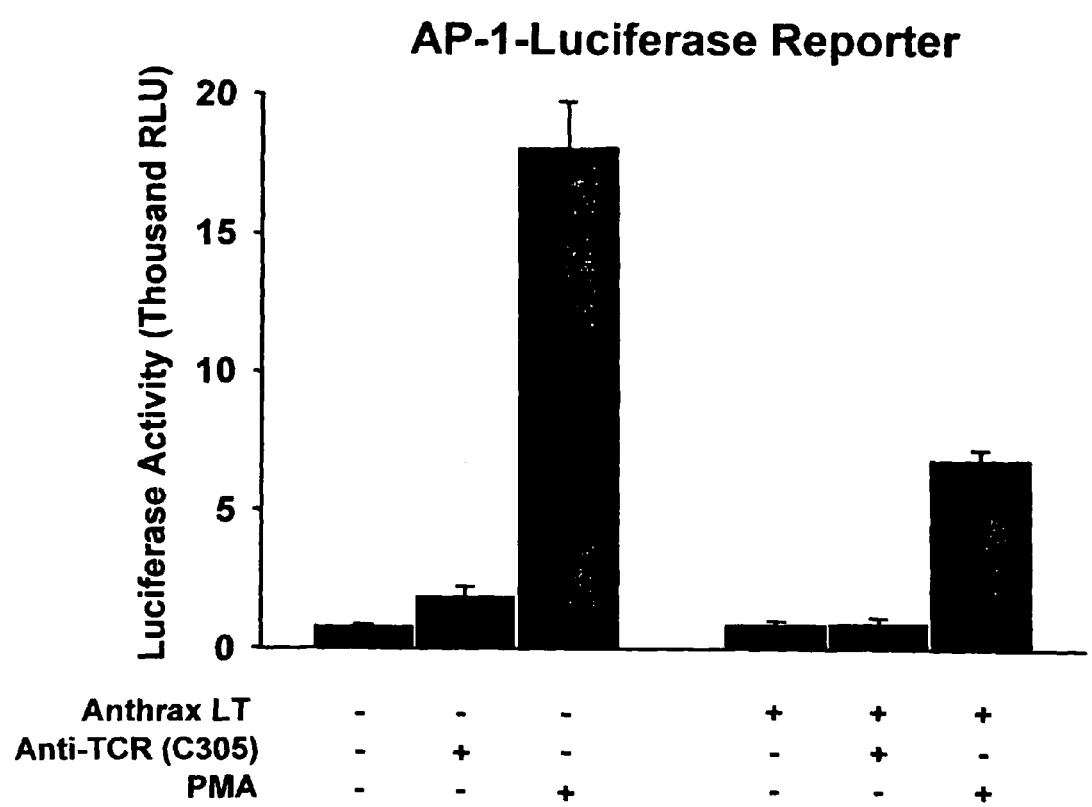
FIG. 1C is a bar graph showing the effect of anthrax LT on TCR- and PMA-induced activity of AP-1. Error shown represents intra-assay standard deviation generated from triplicate samples.

As shown in FIG. 1C, a decrease was observed in the TCR- and PMA-induced activity of an AP-1 reporter construct in anthrax LT-treated Jurkat cells. As AP-1 is a downstream effector in MAPKK/MAPK signaling pathways, these observations are consistent with a specific action of anthrax LT to inactivate MAPKKs in Jurkat cells, thereby disrupting downstream signaling.

EXAMPLE 2

Effect of Anthrax LT on Jurkat Cell Function

This example describes methods used to demonstrate the effect of anthrax LT on a variety of functions of Jurkat cells, such as cell proliferation, signal transduction through the TCR, TCR-dependent calcium mobilization and NF-κB activation.

Jurkat cells were washed with PBS and resuspended at a concentration of $6.25 \times 10^5$ cells/mL in RPMI complete medium in 96 well plates (100 µL/well). Cells were treated with or without LT as described in Example 1, and incubated in a 5% $CO_2$ humidified incubator at 37° C. for various amounts of time.

At the indicated time points, cellular proliferation was measured by MTT using a commercial kit, following the manufacturer's protocol (R&D Systems). Briefly, 10 µl of MTT reagent was added to each well. The cultures were further incubated for 2-4 hours at 37° C. until a purple precipitate was visible under the microscope. Detergent reagent was then added to the wells. The treated cultures were then incubated in the dark at 37° C. for at least 3 hours. Absorbance at 570 nm was measured using a spectrophotometer (Dynatech Lab; Chantilly, Va.). Each MTT assay was performed in triplicate.

Figure 2A:
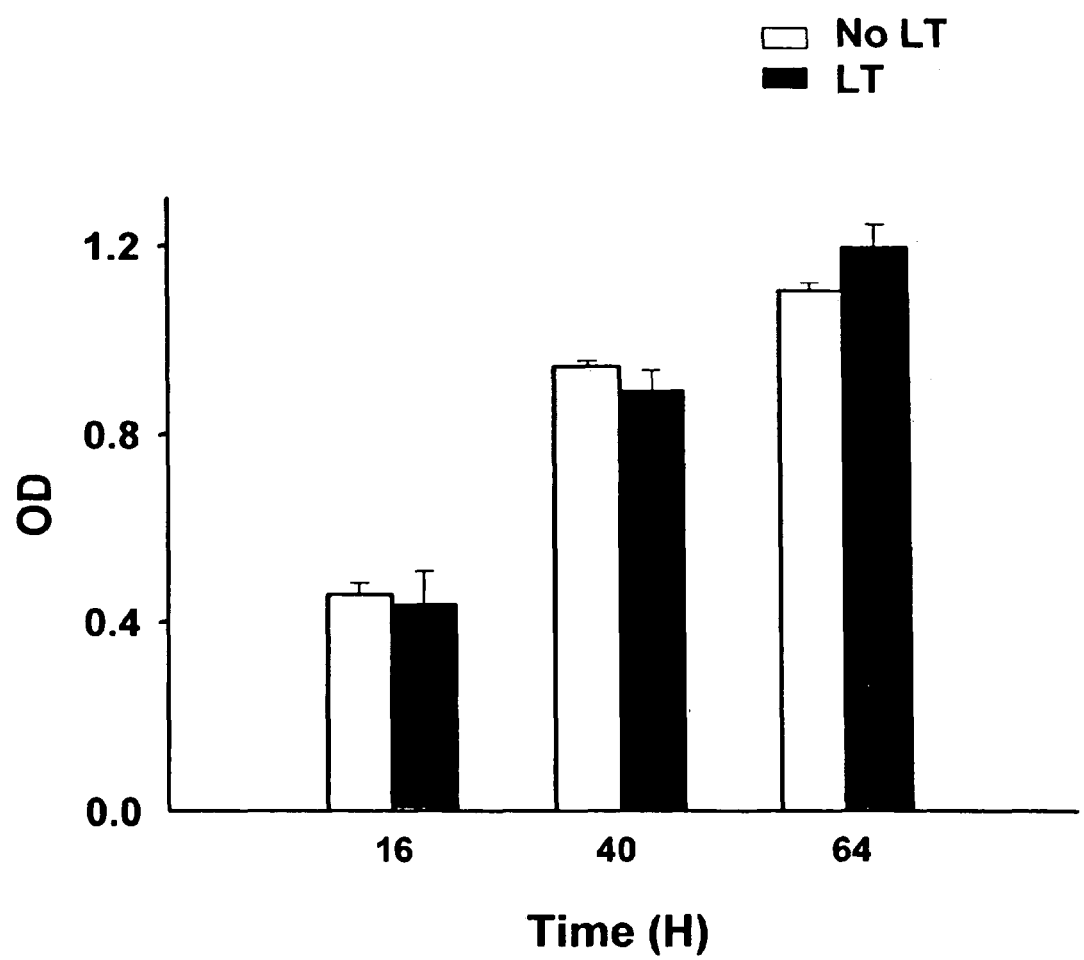
FIG. 2A is a bar graph showing the proliferation rate of Jurkat cells cultured in the presence or absence of anthrax LT. Representative experiments from three separate experiments are shown. Error shown represents intra-assay standard deviation generated from triplicate samples.

As shown in FIG. 2A, there was minimal difference in the proliferation of Jurkat cells cultured in the presence or absence of anthrax LT. Anthrax LT-treated Jurkat cells proliferated at rates greater than 94% of control untreated cultures for up to three days following treatment. Trypan blue exclusion testing of anthrax LT-treated Jurkat cells showed no decrease in the viability compared to untreated cells (>95% normal viability following 48 hours of treatment). In contrast, anthrax LT has been reported to have a pro-apoptotic effect on peripheral blood mononuclear cells (Popov et al., *FEBS Lett.* 527:211, 2002).

Figure 2B:
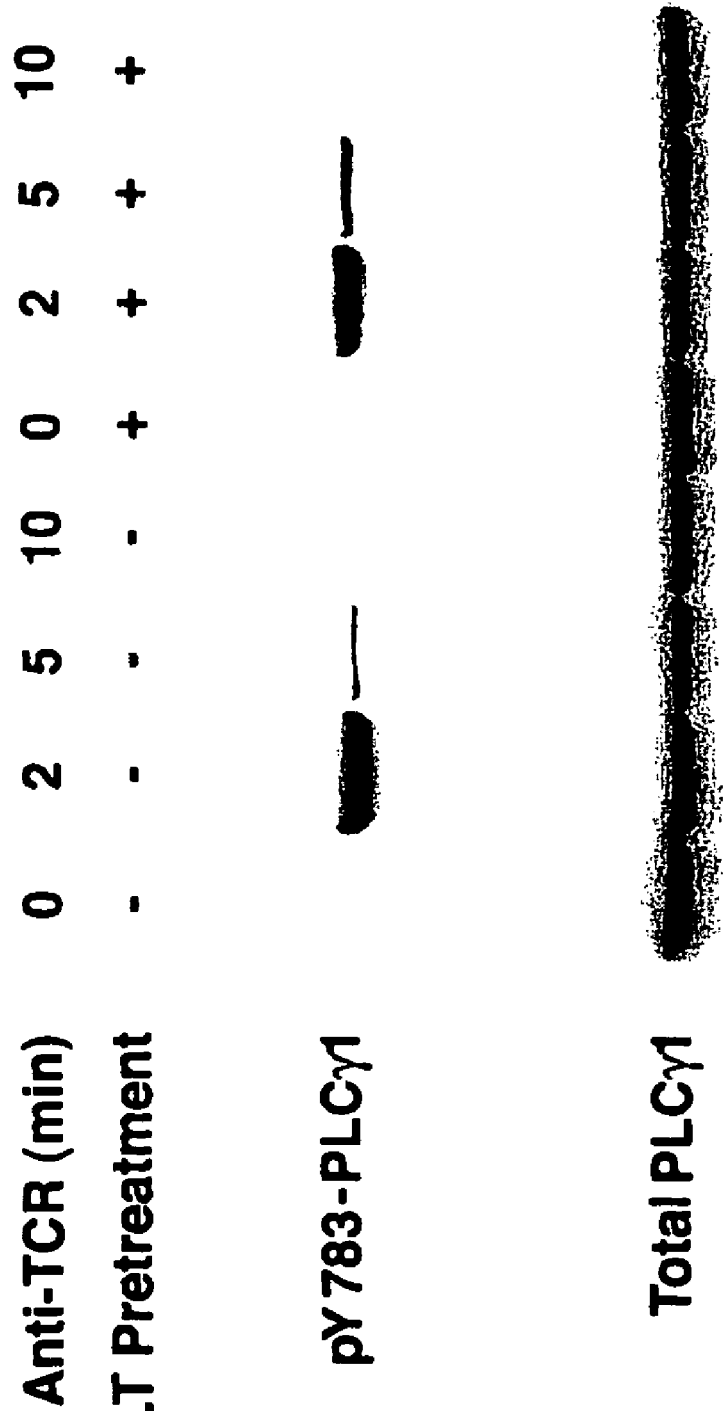
FIG. 2B is a digital image of a Western blot showing levels of pY783-PLC-γ1 (upper panel) and total PLC-γ1 (reblot, lower panel) in Jurkat cells pre-cultured in the presence or absence of anthrax LT and re-stimulated with C305 (a TCR activating antibody) for varying amounts of time. Representative experiments from two separate experiments are shown.

The effect of anthrax LT on signal transduction in Jurkat cells in response to stimulation through the TCR was determined as follows. Jurkat cells were incubated with anthrax LT, and Western blotting performed with anti-phosphotyrosine (4G10), anti-pY783-PLC-γ1 or anti-PLC-γ1 (Cell Signaling Technology; Beverly, Mass.) as described in Example 1. No difference was observed in the pattern of phosphorylated proteins comparing anthrax LT-treated and untreated Jurkat cells treated with a TCR-specific monoclonal antibody agonist (anti-TCR/C305 stimulation, 0/2/5/10 minutes). Similarly, as shown in FIG. 2B, anthrax LT did not affect the TCR-dependent phosphorylation of phospholipase C (PLC)-γ1, a signal transduction factor that is the nexus for several TCR-dependent signaling pathways, ultimately leading to mobilization of intracellular calcium stores and activation of NF-κB and AP-1.

To demonstrate that anthrax LT treatment of Jurkat cells does not affect TCR-induced mobilization of calcium, calcium mobilization assays were performed as follows. Jurkat cells were incubated in RPMI complete medium with or without anthrax LT for three hours. Cells were then harvested, centrifuged, washed, and resuspended in HBSS with 0.5% BSA (Sigma; St. Louis, Mo.). Subsequently, Indo 1/AM (Calbiochem; San Diego, Calif.) was added to a final concentration of 1.8 and this cell suspension was incubated at 37° C. for 30 minutes with continuous agitation. The cells were then washed three times in loading buffer, and resuspended at a ratio of $4 \times 10^6$ cells/2 mL buffer. The cell suspension was passed through a 70 µm filter prior to analysis. Following stimulation with supernatant from the C305 hybridoma, which expresses anti-Jurkat TCR monoclonal antibody (Weiss and Stobo. *J. Exp. Med.* 160:1284, 1984), the ratio of unbound/bound $Ca^{++}$ was measured on a Shimadzu RF 1501 Spectrofluorophotometer (Mandel Scientific Company, Inc.; Guelph, Ontario, Canada).

The effect of anthrax LT on the PMA/ionomycin-induced activity of a transfected NF-κB reporter construct was performed as described in Example 1, except that 5 µg of NF-κB-responsive luciferase construct (pNF-κB-Luc; BD Biosciences, Palo Alto, Calif.) was used to transfect Jurkat cells. Cells were pre-cultured in the presence or absence of anthrax LT and re-stimulated with combined PMA and ionomycin (ionomycin was prepared in DMSO and used at a dose of 5 nM; EMD Biosciences, Inc.; San Diego, Calif.) for 5 hours. Reporter activity was assayed in triplicate using a luminometer.

Figure 2C:
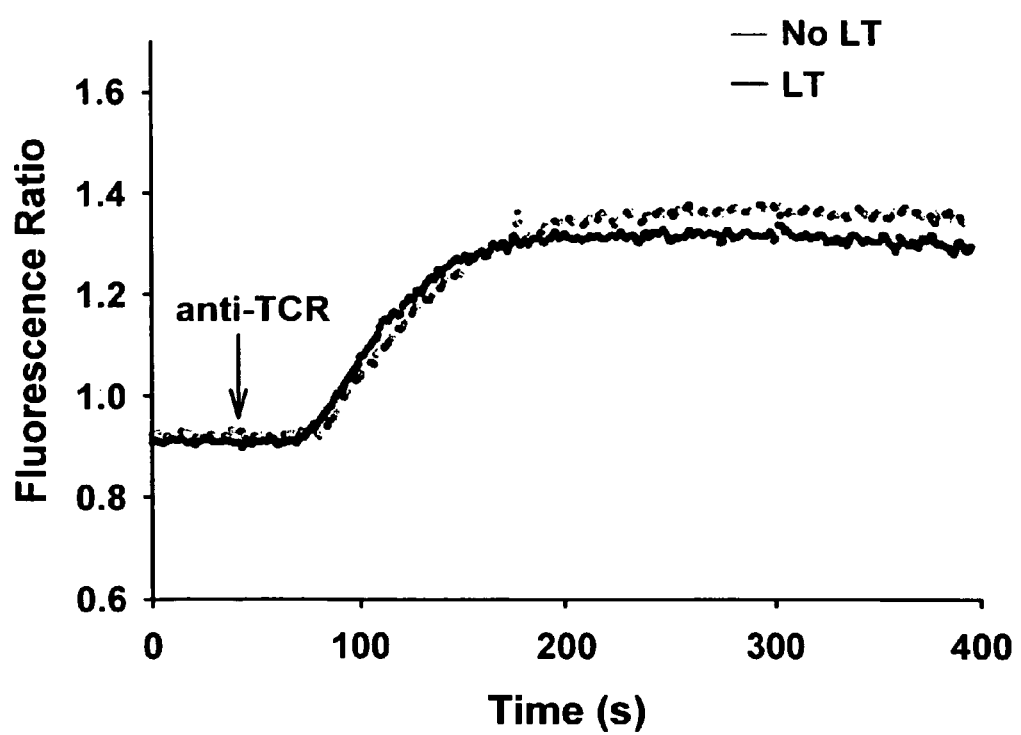
FIG. 2C is a graph showing the relative amount of calcium mobilization in Jurkat cells pre-cultured in the presence or absence of anthrax LT and re-stimulated with C305. Representative experiments from two experiments are shown.
Figure 2D:
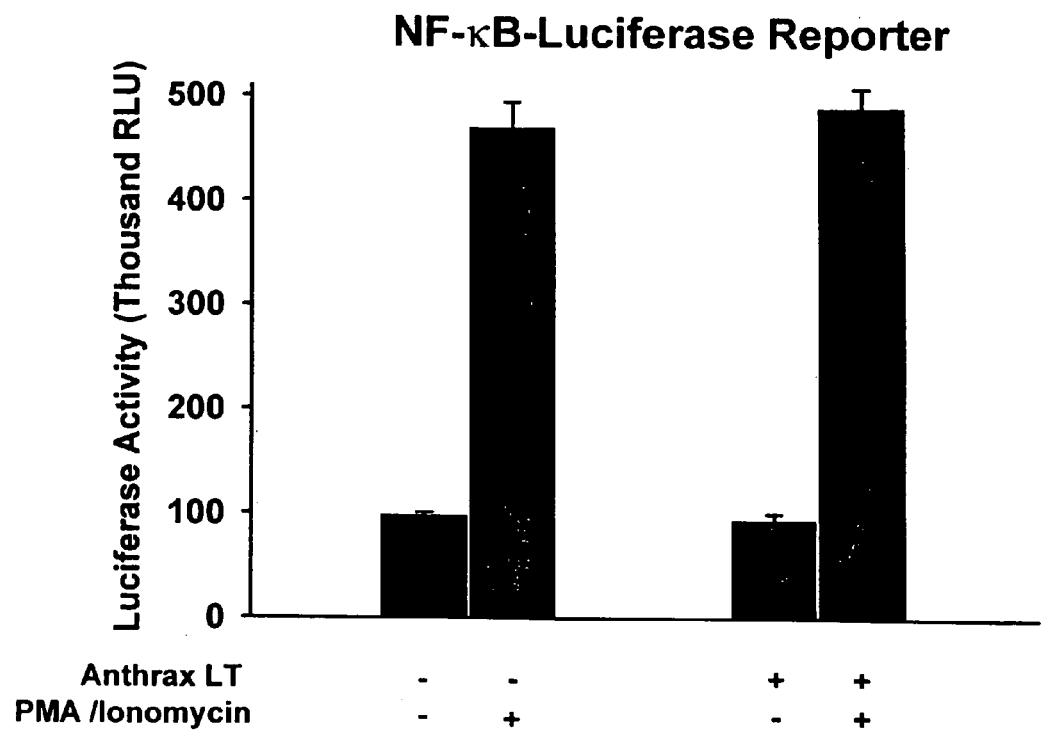

As shown in FIGS. 2C and 2D, anthrax LT treatment of Jurkat cells did not affect TCR-induced mobilization of calcium or PMA/ionomycin-induced activity of a transfected NF-κB reporter construct, indicating that the toxin does not block the signal transduction pathways leading to these downstream effectors.

EXAMPLE 3

Anthrax LT Decreases IL-2 Production in Anti-CD3- and PMA/Ionomycin-Treated Jurkat Cells This example describes methods used to demonstrate that anthrax LT decreases cellular functions of Jurkat cells that depend on MAPKK signaling. Therefore, such activities can be used as indicators of anthrax LT activity.

The production of IL-2 by Jurkat cells in response to stimulation by either anti-TCR (Su et al., Cell 77:727, 1994) or by combined PMA and ionomycin (Whitehurst and Geppert. *J. Immunol.* 156:1020, 1996) involves MAPK signaling. Therefore, the following methods were used to demonstrate that anthrax LT significantly reduces the production of IL-2 by Jurkat cells stimulated through these pathways.

Jurkat cells ($2 \times 10^6$ cells/mL) were cultured in the presence or absence of anthrax LT, anti-TCR, and/or combined PMA and ionomycin as described in the examples above for 24 hours. Cell-free supernatants were then obtained by centrifugation and were assayed neat or diluted according to the manufacturer's protocol. IL-2 levels in culture supernatants were determined by using a commercial ELISA kit (R & D Systems). Absorbance readings were performed using a microplate reader (Dynatech Laboratories; Chantilly, Va.). Each culture was assayed in duplicate or triplicate, with results averaged.

Figure 3A:
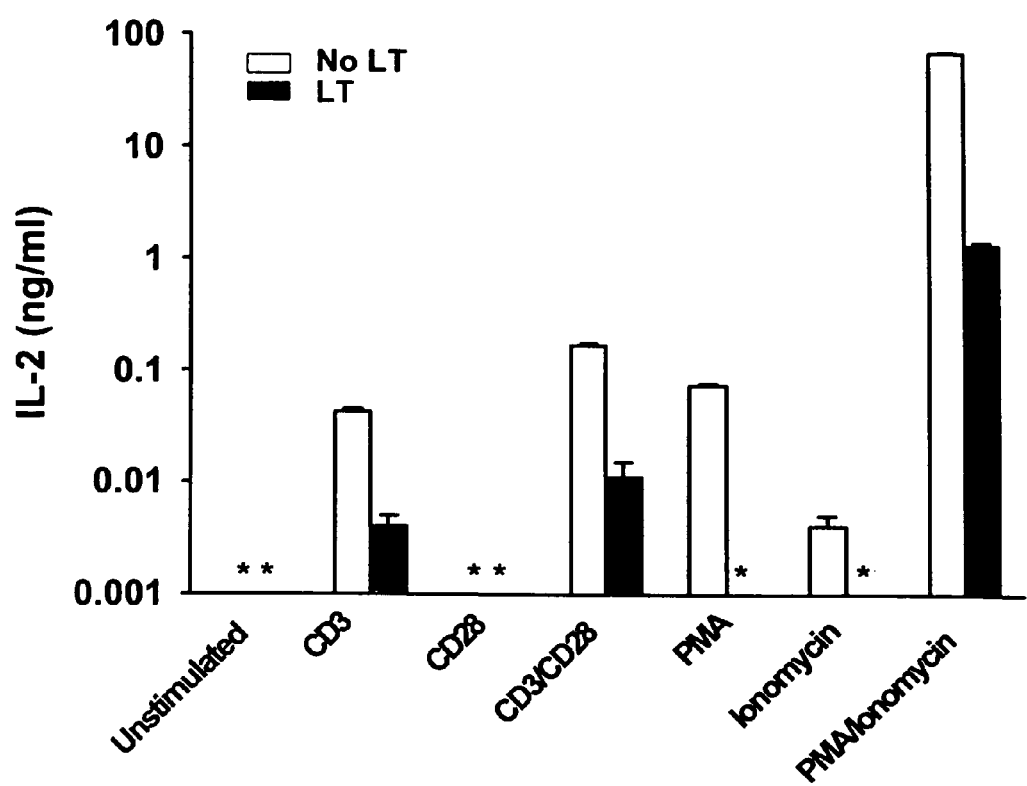
FIG. 3A is a bar graph showing that anthrax LT decreases anti-TCR- and PMA/ionomycin-stimulated IL-2 production in Jurkat cells. Error shown represents intra-assay standard deviation generated from triplicate samples. * indicates none detected

As shown in FIG. 3A, the production of IL-2 by anti-CD3-, PMA-, ionomycin-, or PMA/ionomycin-treated Jurkat cells was greatly reduced subsequent to pre-treatment with anthrax LT.

To determine if this effect on IL-2 production could be reversed in the presence of an inhibitor of LT activity, the following methods were used. Jurkat cells ($1 \times 10^6$/mL) were cultured with PMA and ionomycin in the presence or absence of LT and 0-20 μM of In-2-LF (a specific inhibitor of the protease activity of anthrax LT, Calbiochem, EMD Biosciences, Inc., San Diego, Calif.) for 24 hours in a dose-response experiment. IL-2 levels in culture supernatants were then determined by ELISA as described above. To demonstrate activity of the anthrax LT inhibitor, Jurkat cells were stimulated for 2 h with or without PA, LF, and/or the LT inhibitor (10 μM). Cell lysates were assayed by Western blotting with anti-total MEK-1 and anti-total MEK-2 as described in Example 1.

Figure 3B:
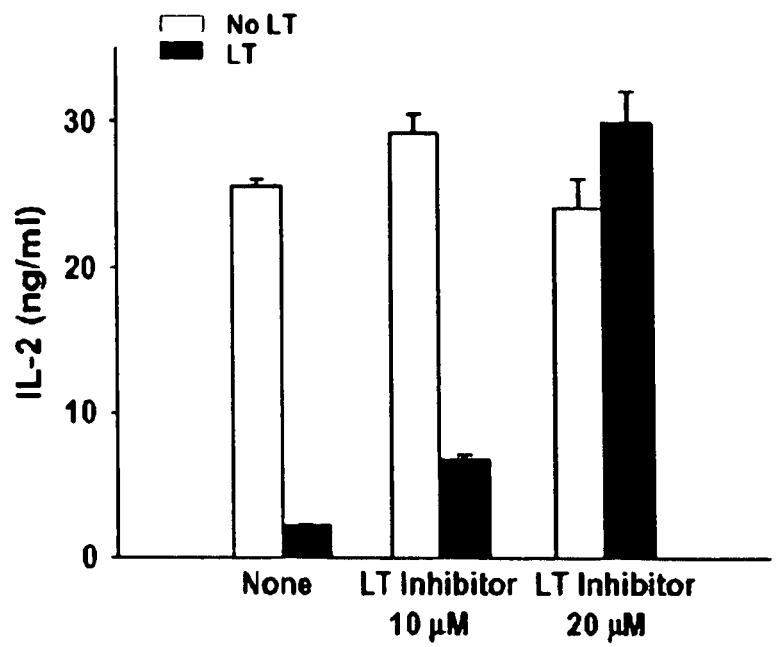
FIG. 3B is a bar graph (upper panel) and western blot (lower panel), showing that an inhibitor of anthrax LT can restore IL-2 production and the presence of MEK-1 and MEK-2. Error shown represents intra-assay standard deviation generated from triplicate samples.
Figure 3B:
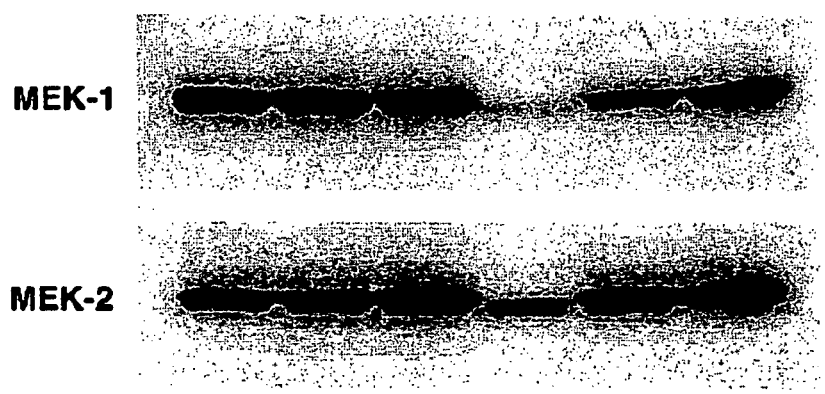

As shown in FIG. 3B, the blockade of IL-2 production by anthrax LT was completely reversed by an inhibitor of the proteolytic action of the toxin on MAPKKs in a dose-dependent manner (FIG. 3B upper and lower panels), confirming the role of this pathway in the IL-2 production blockade.

Figure 3C:
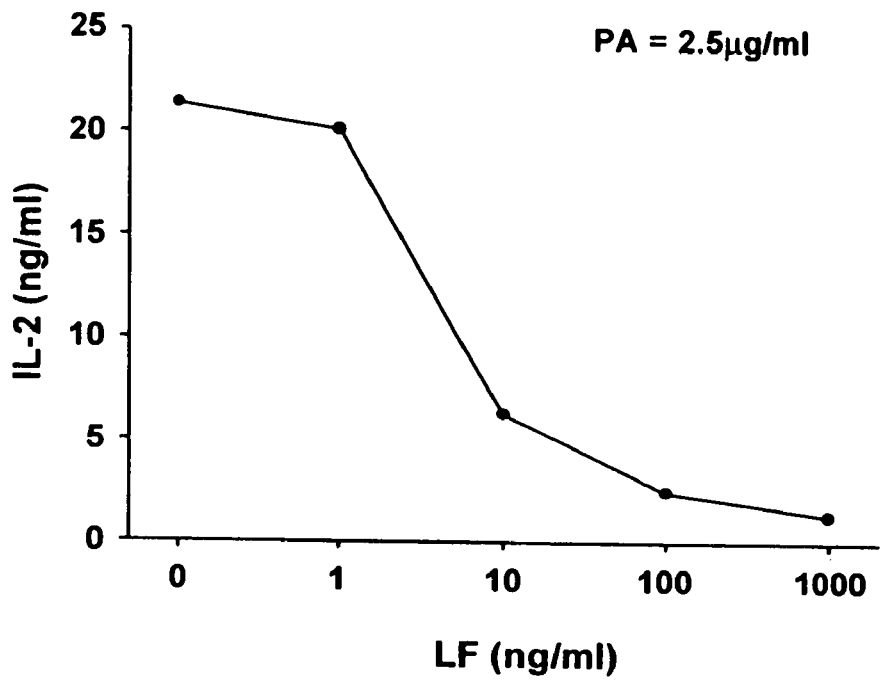
FIG. 3C is a graph showing the dose-dependent effect of anthrax LT on IL-2 production by stimulated Jurkat cells.
Figure 3C:
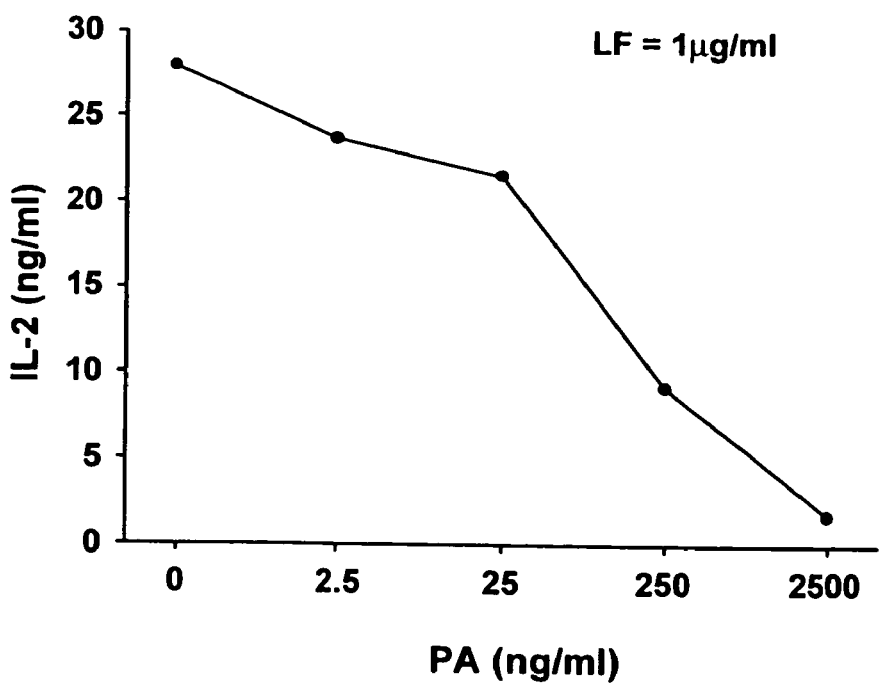

Anthrax LT was shown to have a dose-dependent effect on IL-2 production by stimulated Jurkat cells. Briefly, Jurkat cells ($1 \times 10^6$/mL) were cultured in the presence or absence of a fixed amount of PA (2.5 μg/mL, FIG. 3C upper panel) or LF (1 μg/mL, FIG. 3C lower panel) and variable amounts of LF (FIG. 3C upper panel) or PA (FIG. 3C lower panel) as indicated in FIG. 3C. Cultures were stimulated with PMA and ionomycin for 24 hours, and supernatants were assayed for IL-2 production by ELISA as described above. As shown in FIG. 3C, this effect was detected at a dose as little as 1-10 ng/mL of LF (PA in excess, FIG. 3C upper panel) and 25-250 ng/mL of PA (LF in excess, FIG. 3C lower panel).

EXAMPLE 4

Anthrax LT Decreases Proliferation and IL-2 Production by TCR-Stimulated CD4+ T Cells This example describes methods used to demonstrate that the observations made in Jurkat cells can be extended to primary human CD4+ T cells.

Human CD4+ T cells were prepared from buffy coats from anonymous donors (Department of Transfusion Medicine, Clinical Center, National Institutes of Health; Bethesda, Md.), using a two-step purification procedure. The buffy coat product was incubated for 20 minutes at room temperature with RosetteSep Human CD4+ Cell Enrichment Cocktail (StemCell Technologies; Vancouver, Canada) at a ratio of 20:1. The sample was then diluted with an equal volume of PBS with 2% FBS. CD4+ T cells were isolated by negative selection following separation through a Ficoll gradient (non-CD4+ cells were sedimented).

The CD4+ T cells were positively selected using MACS beads, following the manufacturer's suggested protocol. Briefly, the cells were washed three times with PBS supplemented with 2% FBS, enumerated, and resuspended in MACS buffer. Anti-CD4 MACs beads were added at a ratio of 40 μL per $10^7$ cells. Following column loading, column wash, and elution, the recovered cells were greater than 99.5% CD4+ as assessed by flow cytometry. Human CD4+ T cells were cultured as described in Example 1. Cell viability was determined by propidium iodine staining and FACS analysis.

Levels of MEK-1 and MEK-2 were determined using Western blotting as described in Example 1. Human CD4+ T cells were stimulated with 1 μg/ml of each of anti-human CD3 and/or anti-human CD28 (R&D Systems) for 48 hours with or without LT. Human CD4+ T cells bound FITC-labeled PA in a specific manner. Furthermore, as observed in Jurkat cells (see Example 1), anthrax LT treatment of primary CD4+ T cells led to the rapid proteolysis and reduction of MEK-1 and MEK-2 levels within 3 hours (FIG. 4A, left panel). Anthrax LT suppressed MEK-1 and MEK-2 levels for up to 48 hours, with or without anti-CD3 or anti-CD3/CD28 stimulation (FIG. 4A, right panel).

Figure 4B:
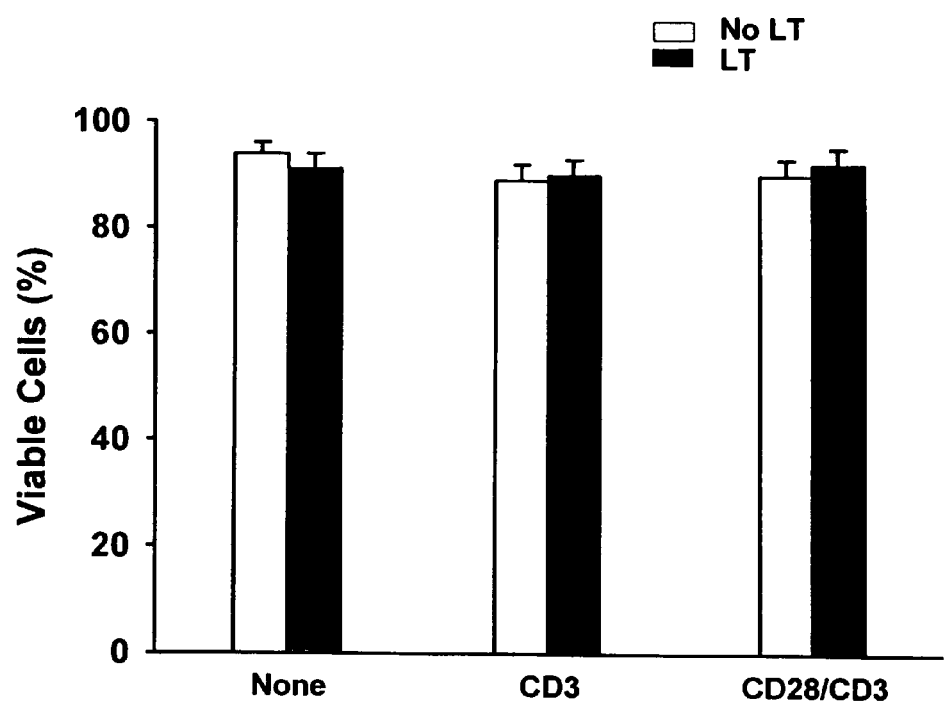
FIG. 4B is a bar graph showing that treatment of purified human $CD4^+$ T cells with anthrax LT does not significantly decrease viability. Data shown represents the results of three separate experiments, with inter-assay standard deviation indicated.

In contrast to certain murine cell lines, treatment of purified human CD4+ T cells with anthrax LT was not associated with decreased viability under these conditions (FIG. 4B).

Proliferation of purified CD4+ T cells cultured in the presence or absence of PMA/ionomycin, anti-CD3, IL-2, and/or anti-CD28 for 48 hours was determined by measuring the incorporation of tritiated thymidine as follows. Culture plates (96 well, Corning Incorporated; Corning, N.Y.) were pre-coated with 1 μg/mL of anti-human CD3 and/or anti-human CD28 (R&D Systems) at 4° C. overnight. Following a PBS wash, $1-5 \times 10^5$ human CD4+ T cells were added to each well in a final volume of 100 μL of complete RPMI. Cells were stimulated as indicated for 48 hours at 37° C., pulsed with 1 μCi of tritiated thymidine (Dupont/NEN Research; Boston, Mass.) overnight, and then processed using a harvester (Perkin Elmer/Wallac; Boston, Mass.). Incorporated tritiated thymidine was measured using a 1205 Betaplate liquid scintillation counter (Perkin Elmer/Wallac; Boston, Mass.). Each proliferation assay was performed in triplicate.

Figure 4C:
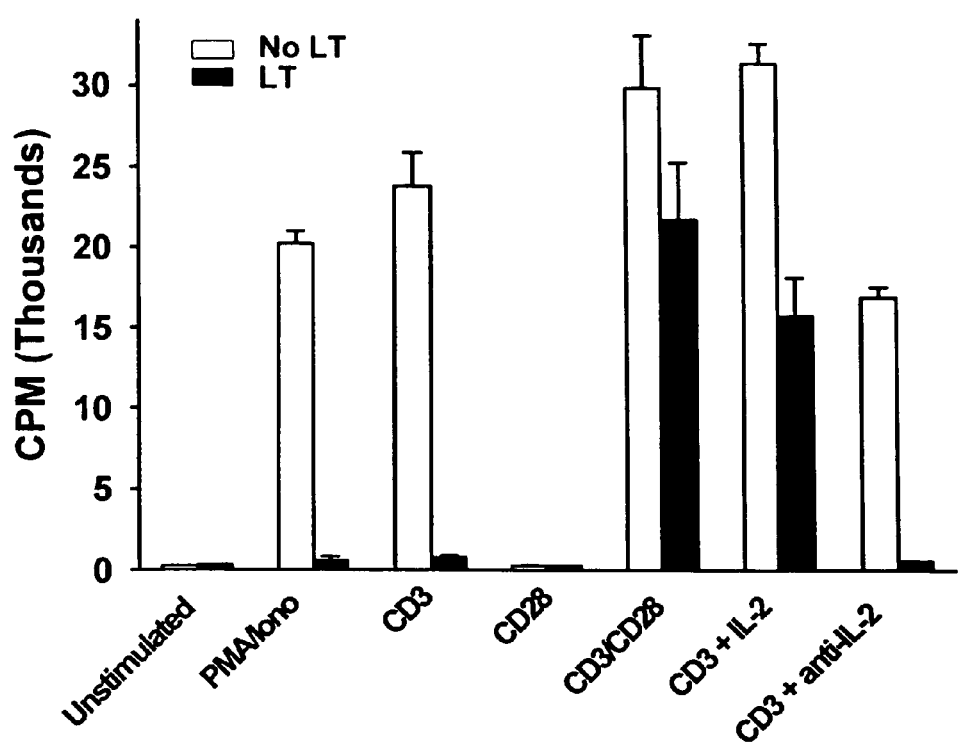
FIG. 4C is a bar graph showing that treatment of purified human $CD4^+$ T cells with anthrax LT significantly decreases anti-CD3- and PMA/ionomycin-induced proliferation. Error shown represents intra-assay standard deviation generated from triplicate samples.

As shown in FIG. 4C, stimulation with anti-CD28 alone did not induce proliferation, but high-level proliferation was detected in CD4+ T cells stimulated with a combination of anti-CD3 and anti-CD28. In addition, anthrax LT treatment decreased anti-CD3- and PMA/ionomycin-induced proliferation by >95%. These results indicate that CD28 signaling overcomes the specific TCR signaling blockade caused by anthrax LT treatment and that anthrax LT is permissive to cell survival and proliferation under some stimulation conditions.

Although it has been reported that serum IL-2 levels are not affected by the treatment of rats with anthrax LT alone (Cui et al., 2004. *Am J Physiol Regul Integr Comp Physiol* 286: R699), the effects of anthrax LT on CD4+ T cells during TCR stimulation conditions have not been previously addressed. In contrast to Jurkat cells, primary CD4+ T cells depend on IL-2 production for normal proliferation in response to TCR stimulation. As IL-2 is positively regulated by MAPK signaling, whether a blockade of IL-2 production was involved in the anthrax LT-induced proliferation blockade was determined. The effect of the addition of exogenous recombinant IL-2 (10 ng/ml; R&D Systems; Minneapolis, Minn.) or neutralizing anti-IL-2 (2 µg/ml; R&D Systems; Minneapolis, Minn.) to anti-CD3-stimulated cultures (1 µg/ml) was determined.

As shown in FIG. 4C, the proliferation rates in the combined IL-2/anti-CD3/anthrax LT-treated CD4+ T cell cultures were not significantly different from those in the combined anti-IL-2/anti-CD3-treated cultures in the absence of anthrax LT (approximately 50% of combined IL-2/anti-CD3-treated cultures). These data indicate a possible relationship between decreased IL-2 production and the anti-proliferative effect of anthrax LT.

Figure 4D:
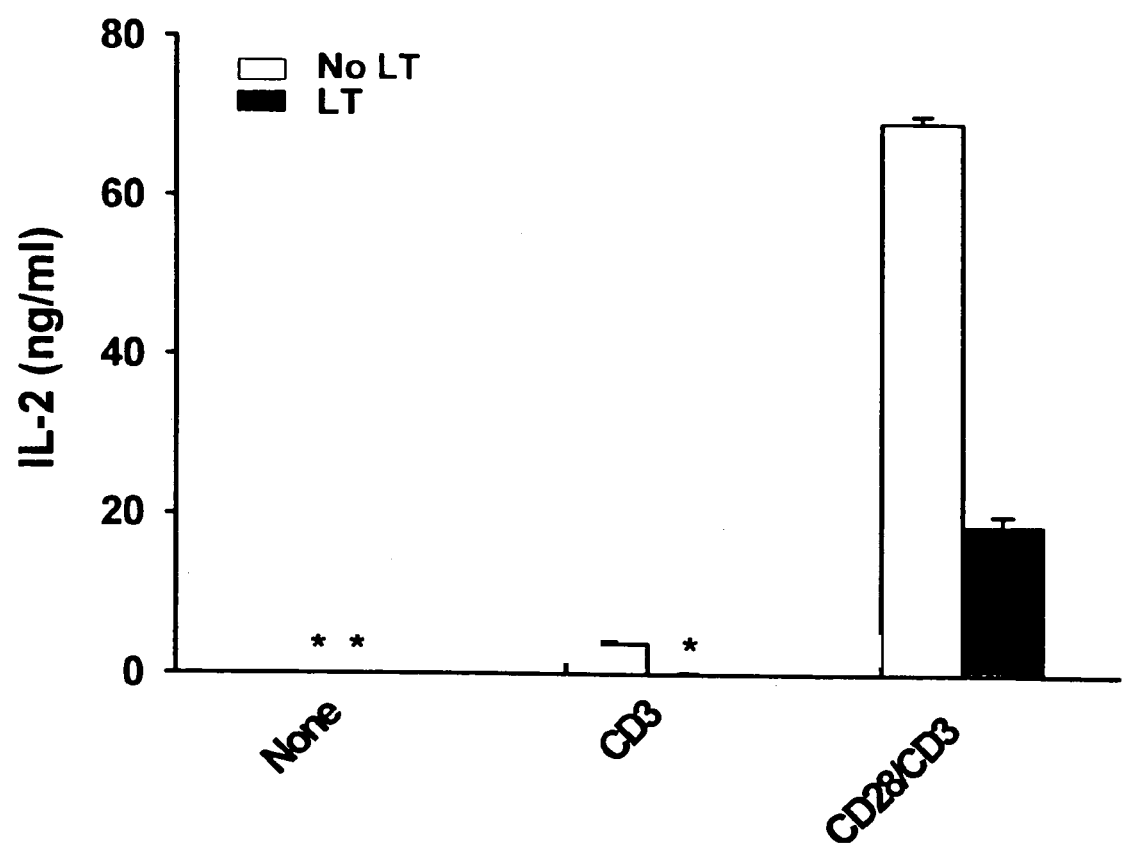
FIG. 4D is a bar graph showing the amount of IL-2 produced in the supernatants of $CD4^+$ T cells cultured in the presence or absence of anthrax LT, anti-CD3, and/or anti-CD28. Error shown represents intra-assay standard deviation generated from triplicate samples. (*:≦30 pg/mL).

To demonstrate the role of anthrax LT in modulating IL-2 production, human CD4+ T cells ($1 \times 10^6$/mL) were stimulated with anti-CD3 with or without anti-CD28. Co-treatment of anthrax LT with anti-CD3-treated CD4+ T cells led to a 97% reduction in the induction of IL-2 to near basal levels (FIG. 4D). Stimulation through the CD28 pathway enhanced IL-2 production in anthrax LT/anti-CD3/anti-CD28-treated cultures, but did not fully correct the IL-2 production deficit (18.6 vs. 69.4 ng/mL in anti-CD3/anti-CD28-treated cultures).

These data demonstrate that anthrax LT significantly decreases TCR-dependent IL-2 production. This effect is specific to the TCR signaling pathway and is not due to a general cytotoxic effect. In addition, the CD28 signaling pathway partially overcomes this blockade.

EXAMPLE 5

Anthrax LT Decreases IL-4 and IFN-γ Production by TCR-Stimulated CD4+ T Cells

The example describes methods used to demonstrate that production of other MAPKK-dependent cytokines by stimulated T cells is decreased in the presence of anthrax LT. Similar methods can be used to measure the production of other MAPKK-dependent cytokines, such as TNF-alpha, IL-1 alpha, IL-1 beta, IL-6, IL-12 and IL-18.

Purified human CD4+ T cells were cultured in the presence or absence of anthrax TL, anti-CD3, or anti-CD3/anti-CD28 using the methods described in Example 4. IFN-γ and IL-4 protein levels in the supernatants of the CD4+ T cells ($1 \times 10^6$/ml) cultured in the presence or absence of anthrax TL, anti-CD3, or anti-CD3/anti-CD28 were determined by ELISA (R & D Systems) as described in Example 4.

Figure 5:
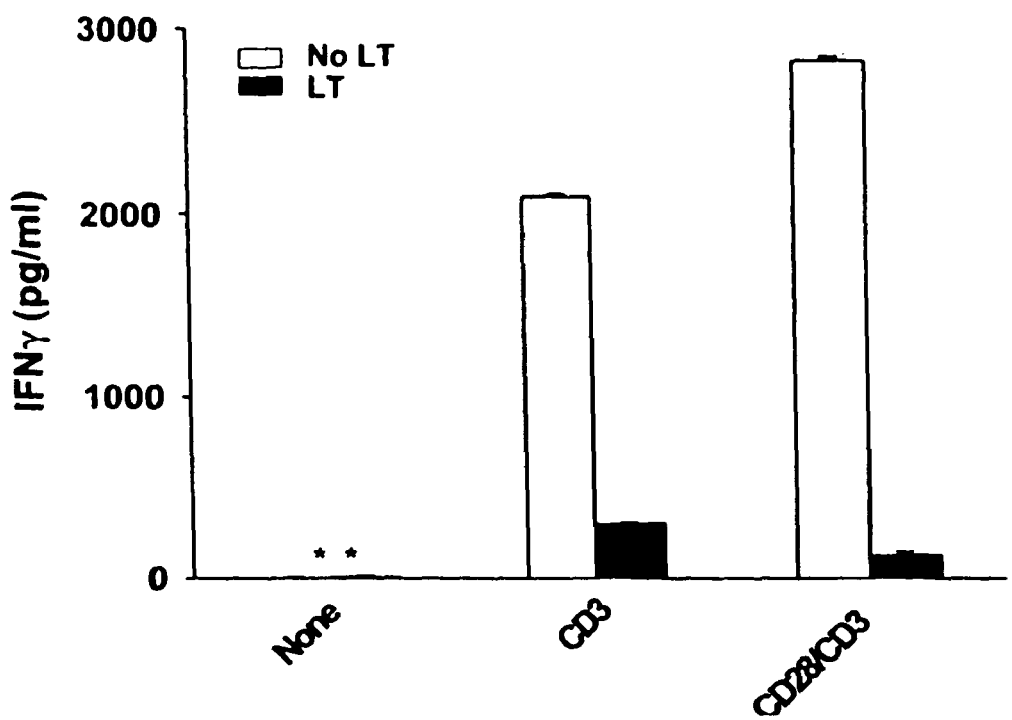
FIGS. 5A and 5B are bar graphs showing the amount of (A) IFN-γ and (B) IL-4 produced in the supernatants of $CD4^+$ T cells cultured in the presence or absence of anthrax LT, anti-CD3, and/or anti-CD28. Error shown represents intra-assay standard deviation generated from triplicate samples. (*:below level of detection).
Figure 5:
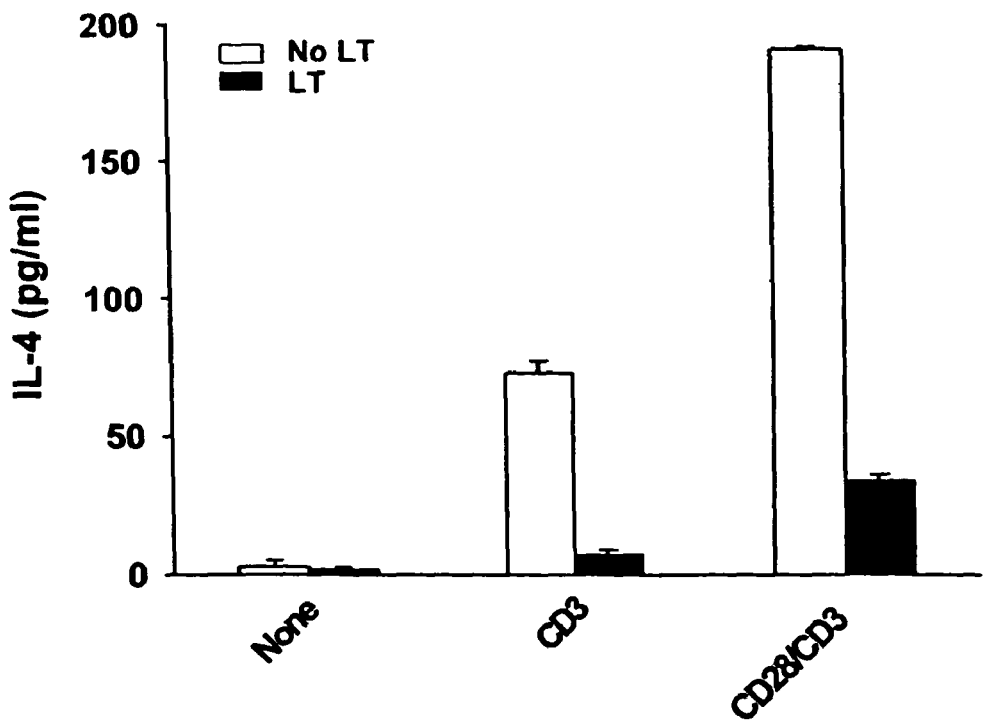

As shown in FIG. 5A, anthrax LT reduced levels of IFN-γ following stimulation with either anti-CD3 (2091±20 vs 306±6 pg/ml) or combined with anti-CD3/anti-CD28 (2827±24 vs. 131±15 pg/ml). Similarly, as shown in FIG. 5B, anthrax TL reduced levels of IL-4 produced by CD4+ T cells following stimulation with either anti-CD3 (73±4 vs 7±2 pg/ml) or combined with anti-CD3/anti-CD28 (191±1 vs. 34±2 pg/ml).

EXAMPLE 6

Anthrax LT Decreases Proliferation of Human B Cells

This example describes methods used to measure proliferation of B cells in response to anthrax LT. In addition, methods are provided for measuring cytokine production by B cells following exposure to LT.

B-cells were isolated using positive or negative selection immunomagnets (Miltenyi), using the manufacturer's protocol. To measure proliferation, the following methods can be used. Purified B-cells are treated with anthrax LT (2.5 µg/mL PA and 1 µg/mL LF) for 0-24 hours (such as 0-180 minutes) and stimulated using standard methods (for example with anti-CD40, or anti-IgM). The effect on B-cell proliferation is determined, for example, by measuring [$^3$H]-uridine incorporation into RNA or [$^3$H]-thymidine incorporation into DNA. For example, cells can be stimulated for 48 hours at 37° C., and then pulsed with 1 µCi of [$^3$H]-thymidine or [$^3$H]-uridine (Dupont/NEN Research; Boston, Mass.) overnight, and then processed using a harvester (Perkin Elmer/Wallac; Boston, Mass.). Incorporated [$^3$H]-thymidine or [$^3$H]-uridine can be measured using a 1205 Betaplate liquid scintillation counter (Perkin Elmer/Wallac; Boston, Mass.). It is expected that in the presence of LT, B-cell proliferation will decrease (and therefore the amount of [$^3$H]-uridine or [$^3$H]-thymidine measured will decrease), as compared to a B-cell not incubated with LT.

To measure immunoglobulin production (IgM, IgG and Ig) as well as IL-6 production, the following methods can be used. Purified B-cells can be incubated in the presence of LT and stimulated as described above. At various time points, cell-free supernatants are obtained, for example by centrifugation. The supernatant can be assayed neat or diluted. Immunoglobulin (such as IgM, IgG and Ig) as well as cytokine production levels (such as IL-6) in culture supernatants can be determined by using ELISA or Western blotting. It is expected that in the presence of LT, immunoglobulin production and production of MAPKK-dependent cytokines (such as IL-6) will decrease (and therefore the amount of immunoglobulin or cytokines measured in the supernatant will decrease), as compared to an amount of such production by a B-cell not incubated with LT.

EXAMPLE 7

In Vitro Bioassays

This example describes exemplary in vitro assays that can be used to determine whether a test agent is a potential anthrax therapeutic, for example to determine the efficacy of a test agent. Such assays can therefore be used to identify therapeutic agents that can decrease the pathogenicity of anthrax, for example agents that can treat a subject having an anthrax infection or protect a subject from infection in the future (prophylaxis). Although examples are provided using lymphocytes and detecting lymphocyte-associated LT activity, one skilled in the art will appreciate that variations to these in vitro assays can be made. For example, different CD4+ T-cell lines and other assays for determining lymphocyte-associated LT activity can be used.

In some examples, the method includes exposing an isolated human lymphocyte, such as a B-cell or T-cell (for example a CD4+ cell or a Jurkat cell) to anthrax LT and contacted one or more test agents. In particular examples, the isolated lymphocyte is first contacted with one or more test agents, followed by exposure to anthrax LT. In other particular examples, the isolated lymphocyte is first exposed to anthrax LT, followed by contact with one or more test agents. In yet another particular example, the isolated lymphocyte is contacted with one or more test agents at the same time as the cells are exposed to anthrax LT.

In some examples, the lymphocyte is a stimulated lymphocyte. In particular examples, the method includes stimulating the lymphocytes, for example following exposure to LT, following exposure to a test agent, or at the same time as exposure to the test agent. For example, T-cells can be stimulated by contacting the cells with an agent that activates the TCR, such as anti-CD3 (alone or in combination with a co-stimulator, such as anti-CD28), or with agents that mimic TCR activation. For example, T-cells can be stimulated by contacting the cell with an agent that mobilizes intracellular stores of calcium (such as ionomycin) and an agent that activates protein kinase C (such as PMA). In particular examples, B-cells are stimulated by contacting isolated B-cells with one or more agents that activate the BCR.

After exposing the lymphocytes to the test agent, LT, and in some examples following stimulation, lymphocyte-associated LT activity is determined. For example, lymphocyte-associated LT activity can be determined by detecting a MAPKK-dependent cytokine response to LT, such as detecting an amount of IL-2, IL-4, IL-6, or IFN-γ, or by determining an amount of lymphocyte proliferation. In particular examples, the method further includes comparing the observed lymphocyte-associated LT activity to a baseline, control, standard curve, or reference value.

In a particular example, the lymphocyte is a Jurkat cell. Jurkat cells in culture are exposed to anthrax LT and contacted with one or more test agents. Subsequently, lymphocyte-associated LT activity is determined, for example by detecting one or more MAPKK-dependent cytokine responses to LT, such as by measuring an amount of MAPKK-dependent cytokine (such as IL-2, IL-4, or IFN-γ) secreted by the Jurkat cell.

In another particular example, the lymphocyte is an isolated primary T-cell, such as a CD4+ T-cell isolated from a human subject. The T-cells in culture are exposed to anthrax LT, contacted with one or more test agents, and stimulated. Subsequently, lymphocyte-associated LT activity is determined, for example by detecting one or more MAPKK-dependent cytokine responses to LT, such as by measuring an amount of MAPKK-dependent cytokine (such as IL-2, IL-4, or IFN-γ) secreted by the T-cell, or by determining an amount of T-cell proliferation.

In yet another particular example, the lymphocyte is an isolated primary B-cell obtained from a human subject. The B-cells in culture are exposed to anthrax LT, contacted with one or more test agents, and stimulated. Subsequently, lymphocyte-associated LT activity is determined, for example by detecting one or more MAPKK-dependent cytokine responses to LT, such as by measuring an amount of MAPKK-dependent cytokine (such as IL-6), or by determining an amount of B-cell proliferation.

In one example, the lymphocytes are exposed to at least 0.1 μg/ml of PA and at least 0.1 μg/ml of LF (for example at a ratio of at least 1:1 of PA:LF) for at least 10 minutes. In a particular example, the test agent includes an antibody that specifically binds to anthrax LT.

In one example, lymphocyte-associated LT activity is determined by measuring an amount of MAPKK-dependent cytokine produced by the lymphocyte (such as an amount of IL-2, IL-4, IL-6, or IFN-γ protein secreted into the cell culture supernatant) using the ELISA assay described in the Examples above. Agents that decrease lymphocyte-associated LT activity, for example by increasing an amount or function of MAPKK-dependent cytokine, such as an increase of at least 20%, at least 50%, at least 75%, or even at least 95%, compared to an amount or function of a MAPKK-dependent cytokine in the absence of the test agent (but in the presence of anthrax LT), can be useful, for example, in treating an anthrax infection (for example reducing one or more symptoms of systemic shock) or decreasing infection by anthrax.

In another example, lymphocyte-associated LT activity is determined by measuring an amount of lymphocyte proliferation using the MTT or [$^3$H]-thymidine assay described in the Examples above. Agents that decrease lymphocyte-associated LT activity, for example by increasing lymphoproliferation, such as an increase of at least 20%, at least 50%, at least 75%, or even at least 95%, compared to an amount of lymphoproliferation in the absence of the test agent (but in the presence of anthrax LT), can be useful, for example, in treating an anthrax infection (for example reducing one or more symptoms of systemic shock) or decreasing infection by anthrax.

In particular examples, lymphocyte-associated LT activity is compared to a baseline, such as the activity present prior to addition of the test agent (or in the absence of the test agent). For example, the activity or amount of MAPKK-dependent cytokine can be compared to the activity or amount present prior to addition of the test agent. In another example, lymphocyte-associated LT activity is compared to a control sample, such as a sample not incubated with the test agent (positive control), or a sample not incubated with the test agent and not infected with anthrax or a sample incubated with an LT neutralizing antibody (negative control). Test agents that decrease lymphocyte-associated LT activity (such as increase the function or amount of MAPKK-dependent cytokine or increase lymphocyte proliferation) relative to the baseline or the positive control, such as a decrease of at least 20%, can be useful, for example, in treating an anthrax infection or decreasing infection by anthrax. Similarly, test agents that have a similar amount of lymphocyte-associated LT activity (such as similar function or amount of MAPKK-dependent cytokine or lymphocyte proliferation) relative to the negative control, such as a change of no more than 10%, can be useful, for example, in treating an anthrax infection or decreasing infection by anthrax.

In yet another example, lymphocyte-associated LT activity is compared to a reference value, such as a standard curve. For example, the reference value can be a number that indicates when lymphocyte-associated LT activity is present or not for a particular experimental value (such as an amount of lymphoproliferation or an amount of MAPKK-dependent cytokine present). An example of a standard curve is a graph plotting an amount of lymphocyte-associated LT activity (such as an amount of lymphoproliferation or an amount of MAPKK-dependent cytokine present) versus an amount of biologically active LT present. Such a graph allows one to extrapolate a measured lymphocyte-associated LT activity to an amount of biologically active LT present, thus permitting identification of test agents with the desired therapeutic activity and efficacy.

Agents identified to be therapeutically useful in vitro can be selected and analyzed for their ability to have similar therapeutic effects in vivo (for example using the methods described in Example 8).

EXAMPLE 8

In Vivo Bioassays

This example describes in vivo methods that can be used to demonstrate in vivo activity of agents originally identified using in vitro assays (such as those described in Example 7). One skilled in the art will appreciate that other in vivo assays can be used. For example, different subjects can be used, and other assays to determine lymphocyte-associated LT activity can be used. In addition, the methods described herein can be used to expose a subject to anthrax (such as infection with *B. anthracis* spores or anthrax LT), and subsequently cells isolated from the subject are cultured and test agents analyzed in vitro, for example using the in vitro methods described in Example 7.

For example, the in vivo method can include infecting an animal with anthrax (for example by exposing the animal to *B. anthracis* spores or anthrax LT) and administering one or more test agents (such as at least one test agent, at least two test agents, or at least three test agents) to the subject, wherein the test agent was previously shown in an in vitro assay to decrease lymphocyte-associated LT activity. The exposure to LT and administration of the one or more test agents can be simultaneous, or one subsequent to the other. Infecting the animal with anthrax can include administering *B. anthracis* spores (such as $10^4$-$10^8$ spores/ml having an MOI of about 1:1) or anthrax toxin (such as LT, for example at a ratio of at least 1:1 of PA:LF, such as at least 2:1 PA:LF) to the subject. Particular exemplary doses are provided below. Subsequently, the lymphocyte-associated LT activity in the subject is determined. For example, a biological sample can be obtained from the subject, such as a blood sample, and the lymphocyte-associated LT activity present in the sample determined.

In one example, lymphocyte-associated LT activity is determined by measuring an amount of MAPKK-dependent cytokine present (such as an amount of IL-2, IL-4, IL-6, or IFN-γ protein secreted into the serum of the subject) in the subject, for example at least 30 minutes following infection, such as at least 1 hour following infection. In addition, lymphocyte-associated LT activity can be determined by measuring an amount of lymphoproliferation (for example, an amount of lymphocytes present in a blood sample of the subject). Agents that decrease lymphocyte-associated LT activity, for example by increasing the function or amount of MAPKK-dependent cytokine, such as an increase of at least 20%, at least 50%, at least 75%, or even at least 95%, can be useful, for example, in treating an anthrax infection (for example reducing one or more symptoms of systemic shock) or decreasing (or preventing) infection by anthrax.

In particular examples, lymphocyte-associated LT activity is compared to a baseline, such as the activity present prior to addition of the test agent (or in the absence of the test agent). For example, the observed MAPKK-dependent cytokine response to LT (such as an amount of lymphoproliferation) can be compared to the observed MAPKK-dependent cytokine response to LT present in the subject prior to addition of the test agent. In another example, lymphocyte-associated LT activity is compared to a control, such as a sample that includes lymphocyte-associated LT activity present in the absence of the test agent and in the presence of anthrax (*B. anthracis* spores or anthrax LT), such as a sample from subject exposed to or infected with anthrax prior to receiving a therapeutic agent (positive control), or a sample that includes lymphocyte-associated LT activity present in the absence of the test agent and anthrax, such as a sample from a subject not infected with or exposed to anthrax (negative control). Test agents that decrease lymphocyte-associated LT activity (such as an increase the function or amount of MAPKK-dependent cytokine or lymphoproliferation) relative to the baseline or the positive control, such as an increase of at least 20%, can be useful, for example, in treating an anthrax infection or decreasing infection by anthrax. Similarly, test agents that have a similar an amount of lymphocyte-associated LT activity (such as similar or increased function or amount of MAPKK-dependent cytokine or lymphoproliferation) relative to the negative control, such as a change of no more than 10%, can be useful, for example, in treating an anthrax infection or decreasing infection by anthrax.

Agents identified to be therapeutically useful in vivo can be selected and analyzed for their ability to have similar therapeutic effects in a human subject, and to determine the therapeutically effective dose.

Exemplary Animals and Doses

Rhesus macaques (*Macaca mulatta*) are the most commonly used nonhuman primate model of human inhalation anthrax exposure. Methods infecting rhesus macaques with *B. anthracis* spores are known (for example see Fritz et al., *Lab. Invest.* 73:691-702, 1995). Briefly, rhesus macaques (such as those at 3-15 kg) are infected with virulent *B. anthracis* spores (such as spores of the Ames strain) via aerosol challenge as follows. The rhesus macaques are exposed in a head-only chamber to a spore aerosol generated by a three-jet Collison nebulizer. For each animal, the concentration of spores in the aerosol inhaled dose (expressed as $LD_{50}$) is determined by plating a sample from an all glass impinger onto trypic soy agar plates. One aerosol $LD_{50}$ in rhesus macaques is $5.5 \times 10^4$ spores. In particular examples, animals infected by aerosol can receive about 5-100 $LD_{50}$ of spores, such as 50-100 $LD_{50}$ of spores. The spores can be diluted in water. The animals can be anesthetized during the infection procedure. Before or after the aerosol challenge, the animal is administered one or more test agents (for example in combination with a pharmaceutically acceptable carrier). A separate group of control animals can be administered phosphate-buffered saline (PBS) as a negative control.

Another model of anthrax infection is the rabbit. Methods of infecting a rabbit with anthrax by inhalation or subcutaneous inoculation are known (for example see Zaucha et al. *Arch. Pathol. Lab. Med.* 122:982-92, 1998). For example, New Zealand white rabbits (*Oryctolagus cuniculus*) can be exposed to *B. anthracis* spores (for example via aerosol or subcutaneous inoculation). For subcutaneous administration, spores of the desired *B. anthracis* strain (such as the Ames strain) can be suspended in a sterile carrier (such as water or PBS) at the desired concentration (for example $10^2$ to $10^5$ CFU at 0.5 ml/dose). The spores are injected into the rabbit, for example in the dorsal interscapular region. For aerosol exposure, the methods described above can be used (for example at a dose of $10^4$ to $10^8$ CFU). In particular examples, rabbits are exposed using a nose-only chamber, instead of a head-only chamber.

Anthrax toxin can also be administered to a subject. Lethal toxin (LT), the combination of LF and PA, is sufficient to induce many of the laboratory manifestations of anthrax disease in animal models. For example Moayeri et al. (*J. Clin. Invest.* 112(5):670-82, 2003) describe administration of toxin to mice. Briefly, BALB/cJ or C57BL/6J mice, such as those 6-8 weeks old, are injected with toxin (such as 50 μg, 100 μg, or 250 μg of each toxin component, LF and PA). For example, in a mouse, volumes that can be used for injection, include, but are not limited to 1 ml intraperitoneally (i.p.) and 10-100 μl intravenously (i.v.).

Similarly, Maynard et al. (*Nat. Biotechnol.* 20:597-601, 2002) describe administration of toxin to Fisher 344 rats. Briefly, Fisher 344 rats (such as those about 200-300 g) are injected with toxin (such as 30-50 μg PA and 5-20 μg LF) in a 200 μl volume, for example via penile vein injection.

EXAMPLE 9

Methods of Diagnosing Anthrax Disease

Based on the observation that anthrax LT levels are inversely correlated with lymphoproliferation and production of MAPKK-dependent cytokines in a dose-dependent manner, this example provides methods of determining an amount of anthrax LT present, which can be used to diagnose an anthrax infection in a subject.

The method of diagnosis includes detecting lymphocyte-associated LT activity (for example as measured by levels of MAPKK-dependent cytokines or levels of lymphoproliferation) in a sample from the subject, wherein an increase in such LT activity indicates that the subject has an anthrax infection or has been exposed to anthrax spores or LT. The subject can be one thought to be infected with *B. anthracis*, or a subject at risk for such infection (such as those that work with livestock, laboratory animals, or human subjects infected with *B. anthracis*).

Methods of obtaining biological samples are known in the art. Any biological sample that could contain lymphocyte-associated LT activity (such as those that could contain IL-2, IL-4, IL-6, or IFN-γ nucleic acid molecules or proteins, or those that contain lymphocytes), or LT itself can be used. Particular examples of biological samples, include, but are not limited to blood, serum, plasma, and tissue biopsies. Methods of obtaining such samples are known in the art.

Methods of detecting lymphocyte-associated LT activity are disclosed herein. However, one skilled in the art will appreciate that other methods can be used. For example, lymphocyte-associated LT activity can be determined by detecting a MAPKK-dependent cytokine response to LT. In a specific example, a serum sample is used to determine an amount of extracellular MAPKK-dependent cytokine present in the subject, such as an amount of IL-2, IL-4, IL-6, or IFN-γ. In another example, lymphocyte-associated LT activity can be determined by measuring an amount of lymphoproliferation. In a specific example, a blood sample (such as a sample containing isolated lymphocytes or a subpopulation thereof) is used to determine an amount of lymphoproliferation, such as an amount of B-cell proliferation or CD4$^+$ T-cell proliferation.

In yet other examples, the sample obtained from the subject, such as serum, is contacted with an isolated lymphocyte, such as a lymphocyte in culture. The resulting lymphocyte-associated LT activity then determined. For example, an amount of MAPKK-dependent cytokine secreted by the lymphocytes, or an amount of lymphoproliferation, can be measured.

In a particular example, the observed lymphocyte-associated LT activity in the subject is compared to a reference value, such as a standard curve. For example, a reference value can be a value (or numerical range) that represents an amount of biologically active LT present relative to a particular experimental value, such as the amount of MAPKK-dependent cytokine present or an amount of lymphoproliferation. By comparing the experimental value measured to the reference standard, the amount of biologically active LT present in the subject can be determined. In another example, the observed lymphocyte-associated LT activity in the subject is compared to a standard curve, such as a standard curve representing an experimental value (such as an amount of MAPKK-dependent cytokine or an amount of lymphoproliferation) in the presence of particular amounts of biologically active LT. This permits a determination of the amount of biologically active LT present in the subject.

In another example, the observed lymphocyte-associated LT activity in the subject is compared to a control, such as a positive or negative control. For example, when comparing lymphocyte-associated LT activity present in the subject to a negative control (such as a sample that includes a reference amount of LT activity expected when a subject is not exposed to anthrax LT, or a sample that includes a reference amount of LT activity expected when a subject is exposed to LT and administered a neutralizing LT antibody), an increase in lymphocyte-associated LT activity compared to the control indicates that the subject is infected with anthrax. Examples of such increases include an increase of at least 20%, at least 50%, or even at least 95% relative to the negative control. When comparing lymphocyte-associated LT activity present in the subject to a positive control (such as a sample that includes a reference amount of LT activity expected when a subject is exposed to anthrax LT), a decrease in lymphocyte-associated LT activity compared to the positive control indicates that the subject is not infected with anthrax. Examples of such decreases include a decrease of at least 20%, at least 50%, or even at least 95% relative to the positive control.

EXAMPLE 10

Methods of Treating Anthrax Disease

Based on the observation that anthrax LT decreases production of MAPKK-dependent cytokines by activated T-cells and decreases proliferation of lymphocytes, the present disclosure provides methods of treating an anthrax infection, for example by decreasing lymphocyte-associated LT activity in the subject. Methods of treatment include methods that reduce one or more symptoms in the subject due to the infection, such as fever, systemic shock, inflammation, or blisters on the skin. However, a complete elimination of symptoms is not required. Treatment methods can also include reducing the presence of biologically active anthrax LT in a subject, for example by reducing or preventing infection by *B. anthracis*.

Lymphocyte-associated LT activity can be decreased, for example by functionally impairing one or more MAPKK-dependent cytokines (such as IL-2, IL-4, IL-6, or IFN-γ) or reducing the amount of one or more MAPKK-dependent cytokines available to participate in the pathogenesis of an anthrax infection. Such amounts can be reduced for example, by interfering with the production of biologically active forms MAPKK-dependent cytokines, or the functional activity of MAPKK-dependent cytokines.

In particular examples, the method includes administering to the subject a therapeutically effective amount of an agent that increases the biological activity of one or more MAPKK-dependent cytokines. When the activity of one or more MAPKK-dependent cytokines is increased, for example by upregulating protein or nucleic acid molecule levels, a reduction in one or more symptoms associated with anthrax infection is achieved. For example, a nucleic acid that encodes a MAPKK-dependent cytokine can therefore be used to increase cellular expression of a MAPKK-dependent cytokine. In particular examples, nucleic acid molecules are administered at a concentration of 1-10 mg nucleic acid molecule/kg of subject, such as 1-5 mg/kg, or 3-7 mg/kg. In another example, a MAPKK-dependent cytokine protein (or functional fragment thereof) is administered to a subject. In particular examples, proteins are administered at a concentration of at least 0.1 µg protein/kg of subject, such as at least 10 µg/kg of subject. In one example, about 50 mcg/m$^2$ (Actimmune, IFN-γ) or about 3 million units/m$^2$ (IL-2) is administered to the subject.

Lymphocyte-associated LT activity can also be decreased, for example, by increasing an amount of lymphoproliferation. For example, lymphoproliferation can be increased for example, by administering to the subject an agent that stimulates TCR or BCR, or an agent that mimics such stimulation.

Other exemplary agents are those identified using the methods described in the Examples above. These agents, such as antibodies, peptides, nucleic acid molecules, organic or inorganic compounds, can be administered to a subject in a therapeutically effective amount. After the agent has produced an effect (for example at least one symptom associated with anthrax infection decreases), for example after 24-48 hours, the subject can be monitored for symptoms associated with the infection.

Therapeutic agents can be administered alone, or with a pharmaceutically acceptable carrier. Furthermore, the pharmaceutical compositions or methods of treatment can be administered in combination with (such as before, during, or following) other therapeutic treatments, such as other anti-anthrax agents. In one example, the subject is a mammal, such as a mouse, non-human primate, or human.

EXAMPLE 11

Pharmaceutical Compositions and Modes of Administration

This example provides exemplary methods that can be used to administer agents to an isolated cell in culture, or a subject.

Methods for administering *B. anthracis* spores are known in the art, and can include aerosol inhalation, injection (such as subcutaneous, intramuscular, intravenous, or intraperitoneal). Similarly, methods of administering one or more test agents or a therapeutic agent to a subject are known. Methods of introduction include, but are not limited to, topical, intradermal, intramuscular, intraperitoneal, intravenous, subcutaneous, intranasal, and oral routes.

In an example in which a nucleic acid molecule is the test agent (or therapeutic molecule), such as a cDNA molecule, any method known in the art can be used. Particular examples include delivering the nucleic acid molecule intracellularly (for example by receptor-mediated mechanisms), by an expression vector administered so that it becomes intracellular (for example by use of a retroviral vector, see U.S. Pat. No. 4,980,286), by injection of the nucleic acid molecule to a cell, by use of microparticle bombardment (such as a gene gun; Biolistic, Dupont), coating the nucleic acid molecule with lipids or cell-surface receptors or transfecting agents, or by administering it in linkage to a homeobox-like peptide known to enter the nucleus (for example Joliot et al., *Proc. Natl. Acad. Sci. USA* 1991, 88:1864-8). The present disclosure includes all forms of nucleic acid molecule delivery, including synthetic oligos, naked DNA, plasmid and viral, integrated into the genome or not.

The *B. anthracis* spores, anthrax LT, or test agent can be administered to an animal or an isolated cell in the presence of a pharmaceutically acceptable carrier. *Remington's Pharmaceutical Sciences*, by Martin, Mack Publishing Co., Easton, Pa., 15th Edition (1975), describes compositions and formulations suitable for pharmaceutical delivery of the agents herein disclosed. In general, the nature of the carrier will depend on the mode of administration employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

The amount of therapeutic agent effective in treating or preventing infection by anthrax can depend on the nature of the anthrax and its associated disorder or condition, and can be determined by standard clinical techniques. In addition, in vitro and in vivo assays can be employed to identify optimal dosage ranges, such as the assays described in Examples 7 and 8. For example, effective doses can be extrapolated from dose-response curves derived from in vitro or animal model test systems. The precise dose to be employed in the formulation will also depend on the route of administration, and the seriousness of the disease or disorder, and should be decided according to the judgment of the practitioner and each subject's circumstances.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of identifying an agent that decreases pathogenicity of anthrax, comprising:
    exposing isolated lymphocytes to anthrax lethal toxin (LT);
    contacting the lymphocytes with a test agent; and
    detecting lymphocyte-associated LT activity, wherein detecting lymphocyte-associated LT activity comprises:
        detecting a mitogen-activated protein kinase kinase (MAPKK)-dependent cytokine response of the lymphocytes to the LT, wherein an increased MAPKK-dependent cytokine response in the presence of the test agent indicates that the lymphocyte-associated LT activity is decreased and that the test agent decreases pathogenicity of anthrax; or determining whether there is an increase in proliferation of the lymphocytes, wherein an increase in lymphocyte proliferation in the presence of the test agent indicates that the lymphocyte-associated LT activity is decreased and that the test agent decreases pathogenicity of anthrax.

2. The method of claim 1, wherein exposing the isolated lymphocytes to LT comprises exposing the lymphocytes to purified LT.

3. The method of claim 1, wherein exposing the isolated lymphocytes to LT comprises exposing the lymphocytes to an organism that produces LT.

4. The method of claim 3, wherein exposing the isolated lymphocytes to an organism that produces LT comprises exposing the lymphocytes to Bacillus anthracis (B. anthracis).

5. The method of claim 1, wherein exposing the isolated lymphocytes to LT comprises exposing the lymphocytes to B. anthracis spores.

6. The method of claim 1, wherein the isolated lymphocytes are stimulated lymphocytes.

7. The method of claim 1, wherein the method further comprises stimulating the isolated lymphocytes following exposing the lymphocytes to anthrax LT.

8. The method of claim 7, wherein the isolated lymphocytes are isolated T-lymphocytes, and stimulating the T-lymphocytes comprises contacting the T-lymphocytes with an agent that activates a T-cell receptor (TCR).

9. The method of claim 7, wherein the isolated lymphocytes are isolated T-lymphocytes, and stimulating the T-lymphocytes comprises contacting the T-lymphocytes with 12-O tetradecanoylphorbol 13-acetate (PMA) and ionomycin.

10. The method of claim 7, wherein the isolated lymphocytes are isolated B-lymphocytes, and stimulating the B-lymphocytes comprises contacting the B-lymphocytes with an agent that activates a B-cell receptor (BCR).

11. The method of claim 7, wherein the isolated lymphocytes are first contacted with the LT, and subsequently the lymphocytes are contacted with the test agent and stimulated, wherein a decrease in lymphocyte-associated LT activity indicates the test agent is a therapeutic agent that can be used to treat an anthrax infection.

12. The method of claim 11, wherein the isolated lymphocytes are contacted with the test agent during or before stimulating the lymphocytes, wherein a decrease in lymphocyte-associated LT activity indicates the test agent is a therapeutic agent that can be used to treat an anthrax infection.

13. The method of claim 1, wherein the method further comprises comparing the detected lymphocyte-associated LT activity to a baseline or a control.

14. The method of claim 1, wherein the method further comprises comparing the lymphocyte-associated LT activity in the lymphocyte to a standard curve, wherein the standard curve represents an amount of lymphocyte-associated LT activity versus an amount of biologically active LT present.

15. The method of claim 1, wherein the method further comprises:

selecting an agent that decreased lymphocyte-associated LT activity;

administering the agent that decreased lymphocyte-associated LT activity to a subject; and detecting lymphocyte-associated LT activity in the subject, wherein decreased lymphocyte associated LT activity indicates the test agent decreases pathogenicity of anthrax.

16. The method of claim 15, wherein detecting lymphocyte-associated LT activity in the subject comprises determining whether lymphocyte-associated LT activity is decreased in a sample obtained from the subject.

17. The method of claim 1, wherein the test agent comprises an inhibitor of lymphocyte-associated LT activity.

18. The method of claim 1, wherein the agent that decreases pathogenicity of anthrax is an anti-anthrax therapeutic agent.

19. The method of claim 1, wherein the isolated lymphocytes are isolated human lymphocytes.

20. The method of claim 1, wherein the lymphocytes comprise stimulated human lymphocytes; and wherein an increase in human lymphocyte proliferation or secretion of a MAPKK-dependent cytokine relative to a negative control indicates the test agent decreases pathogenicity of anthrax.

21. The method of claim 1, wherein detecting a MAPKK-dependent cytokine response of the lymphocyte to the LT comprises detecting IL-2.

22. The method of claim 1, wherein detecting a MAPKK-dependent cytokine response of the lymphocyte to the LT comprises detecting IL-4.

23. The method of claim 1, wherein detecting a MAPKK-dependent cytokine response of the lymphocyte to the LT comprises detecting IFN-γ.

24. The method of claim 1, wherein detecting a MAPKK-dependent cytokine response of the lymphocyte to the LT comprises detecting TNF-α, IL-1α, IL-1β, IL-2, IL-4, IL-6, IL-12, IL-18, IFN-γ, or combinations thereof.

25. The method of claim 7, wherein determining whether there is an increase in proliferation of the lymphocytes, comprises measuring proliferation of a stimulated B-cell or T-cell.

26. The method of claim 1, wherein the method is conducted in vitro.

27. The method of claim 19, wherein the isolated human lymphocytes comprise isolated human T-cells.

28. The method of claim 27, wherein the isolated human T-cells comprise isolated human CD4$^+$ T-cells.

29. The method of claim 19, wherein the isolated human lymphocytes comprise isolated human B-cells.

30. The method of claim 1, wherein the isolated lymphocytes comprise lymphocytes isolated from a human blood sample.

31. The method of claim 1, wherein the isolated lymphocytes comprise a human lymphocyte cell line.

32. The method of claim 31, wherein the human lymphocyte cell line comprises human Jurkat cells.

* * * * *